(12) United States Patent
Leuck et al.

(10) Patent No.: US 12,213,717 B2
(45) Date of Patent: Feb. 4, 2025

(54) COMBINATION ULTRASONIC AND ELECTROSURGICAL INSTRUMENT HAVING ELECTRICAL CIRCUITS WITH SHARED RETURN PATH

(71) Applicant: Cilag GmbH International, Zug (CH)

(72) Inventors: Stephen M. Leuck, Milford, OH (US); Eitan T. Wiener, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 768 days.

(21) Appl. No.: 17/337,885

(22) Filed: Jun. 3, 2021

(65) Prior Publication Data
US 2021/0353350 A1     Nov. 18, 2021

Related U.S. Application Data

(63) Continuation of application No. 15/967,740, filed on May 1, 2018, now Pat. No. 11,234,750.
(Continued)

(51) Int. Cl.
*A61B 17/32* (2006.01)
*A61B 18/00* (2006.01)
(Continued)

(52) U.S. Cl.
CPC ...... *A61B 18/00* (2013.01); *A61B 17/320092* (2013.01); *A61B 18/1206* (2013.01);
(Continued)

(58) Field of Classification Search
CPC ............ A61B 17/320092; A61B 18/00; A61B 18/1206; A61B 18/1445;
(Continued)

(56) References Cited

U.S. PATENT DOCUMENTS

| 5,322,055 A | 6/1994 | Davison et al. |
| 5,400,267 A | 3/1995 | Denen et al. |

(Continued)

FOREIGN PATENT DOCUMENTS

| CN | 103040520 A | 4/2013 |
| CN | 104218420 A | 12/2014 |

(Continued)

OTHER PUBLICATIONS

European Examination Report dated Apr. 21, 2021 for Application No. EP 18730577.6, 5 pgs.
(Continued)

*Primary Examiner* — Khadijeh A Vahdat
(74) *Attorney, Agent, or Firm* — Frost Brown Todd LLP

(57) ABSTRACT

A surgical instrument includes a shaft, an ultrasonic transducer, a waveguide acoustically coupled with the ultrasonic transducer and extending distally through the shaft, and an end effector arranged at a distal end of the shaft. The end effector includes an ultrasonic blade acoustically coupled with the waveguide, a clamp arm movable relative to the ultrasonic blade for clamping tissue, and an RF electrode operable to seal tissue with RF energy. The ultrasonic transducer is operable to drive the waveguide and the ultrasonic blade with ultrasonic energy. The surgical instrument further includes an ultrasonic electrical circuit operable to energize the ultrasonic transducer, and an RF electrical circuit operable to deliver RF energy to the RF electrode. A return path of the ultrasonic electrical circuit and a return path of the RF electrical circuit pass through a shared electrically conductive element.

20 Claims, 12 Drawing Sheets

Related U.S. Application Data

(60) Provisional application No. 62/509,351, filed on May 22, 2017.

(51) Int. Cl.
*A61B 18/12* (2006.01)
*A61B 18/14* (2006.01)
*A61B 17/00* (2006.01)
*A61B 17/29* (2006.01)
*A61B 90/00* (2016.01)

(52) U.S. Cl.
CPC .............. *A61B 18/1445* (2013.01); *A61B 2017/00017* (2013.01); *A61B 2017/00137* (2013.01); *A61B 2017/2929* (2013.01); *A61B 2017/2932* (2013.01); *A61B 2017/320072* (2013.01); *A61B 2017/320074* (2017.08); *A61B 2017/320075* (2017.08); *A61B 2017/320078* (2017.08); *A61B 2017/320088* (2013.01); *A61B 2017/320094* (2017.08); *A61B 2017/320095* (2017.08); *A61B 2018/00077* (2013.01); *A61B 2018/00083* (2013.01); *A61B 2018/00607* (2013.01); *A61B 2018/0063* (2013.01); *A61B 2018/00988* (2013.01); *A61B 2018/00994* (2013.01); *A61B 2018/126* (2013.01); *A61B 2018/1452* (2013.01); *A61B 2018/1457* (2013.01); *A61B 2090/0803* (2016.02)

(58) Field of Classification Search
CPC ........... A61B 2017/00017; A61B 2017/00137; A61B 2017/00738; A61B 2017/00929; A61B 2017/2929; A61B 2017/2932; A61B 2017/320072; A61B 2017/320074; A61B 2017/320075; A61B 2017/320078; A61B 2017/320088; A61B 2017/320094; A61B 2017/320095; A61B 2018/00077; A61B 2018/00083; A61B 2018/00136; A61B 2018/00178; A61B 2018/00577; A61B 2018/00607; A61B 2018/0063; A61B 2018/00988; A61B 2018/00994; A61B 2018/126; A61B 2018/142; A61B 2018/1452; A61B 2018/1457
See application file for complete search history.

(56) References Cited

U.S. PATENT DOCUMENTS

| | | | |
|---|---|---|---|
| 5,792,135 A | 8/1998 | Madhani et al. |
| 5,817,084 A | 10/1998 | Jensen |
| 5,873,873 A | 2/1999 | Smith et al. |
| 5,878,193 A | 3/1999 | Wang et al. |
| 5,944,737 A | 8/1999 | Tsonton et al. |
| 5,980,510 A | 11/1999 | Tsonton et al. |
| 6,231,565 B1 | 5/2001 | Tovey et al. |
| 6,283,981 B1 | 9/2001 | Beaupre |
| 6,309,400 B2 | 10/2001 | Beaupre |
| 6,325,811 B1 | 12/2001 | Messerly |
| 6,364,888 B1 | 4/2002 | Niemeyer et al. |
| 6,423,082 B1 | 7/2002 | Houser et al. |
| 6,500,176 B1 | 12/2002 | Truckai et al. |
| 6,773,444 B2 | 8/2004 | Messerly |
| 6,783,524 B2 | 8/2004 | Anderson et al. |
| 6,976,969 B2 * | 12/2005 | Messerly ....... A61B 17/320092 601/2 |
| 7,108,695 B2 | 9/2006 | Witt et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,524,320 B2 | 4/2009 | Tierney et al. |
| 7,691,098 B2 | 4/2010 | Wallace et al. |
| 7,806,891 B2 | 10/2010 | Nowlin et al. |
| 8,025,630 B2 | 9/2011 | Murakami et al. |
| 8,057,498 B2 | 11/2011 | Robertson |
| 8,058,771 B2 | 11/2011 | Giordano et al. |
| 8,147,488 B2 | 4/2012 | Masuda |
| 8,461,744 B2 | 6/2013 | Wiener et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,591,536 B2 | 11/2013 | Robertson |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,663,220 B2 | 3/2014 | Wiener et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,939,974 B2 | 1/2015 | Boudreaux et al. |
| 8,986,302 B2 | 3/2015 | Aldridge et al. |
| 9,017,326 B2 | 4/2015 | DiNardo et al. |
| 9,039,690 B2 | 5/2015 | Kersten et al. |
| 9,039,720 B2 | 5/2015 | Madan |
| 9,089,327 B2 | 7/2015 | Worrell et al. |
| 9,095,367 B2 | 8/2015 | Olson et al. |
| 9,101,385 B2 | 8/2015 | Shelton, IV et al. |
| 9,107,690 B2 | 8/2015 | Bales, Jr. et al. |
| 9,161,803 B2 | 10/2015 | Yates et al. |
| 9,237,921 B2 | 1/2016 | Messerly et al. |
| 9,301,759 B2 | 4/2016 | Spivey et al. |
| 9,402,682 B2 | 8/2016 | Worrell et al. |
| 9,545,253 B2 | 1/2017 | Worrell et al. |
| 9,572,622 B2 | 2/2017 | Shelton, IV et al. |
| 9,681,912 B2 | 6/2017 | Tsubuku et al. |
| 9,724,120 B2 | 8/2017 | Faller et al. |
| 9,750,521 B2 | 9/2017 | Lamping et al. |
| 9,795,436 B2 | 10/2017 | Yates et al. |
| 9,877,720 B2 | 1/2018 | Worrell et al. |
| 9,901,754 B2 | 2/2018 | Yamada |
| 9,949,785 B2 | 4/2018 | Price et al. |
| 9,962,222 B2 | 5/2018 | Brustad et al. |
| 10,010,340 B2 | 7/2018 | Hibner et al. |
| 10,028,765 B2 | 7/2018 | Hibner et al. |
| 10,039,595 B2 | 8/2018 | Sakaguchi et al. |
| 10,092,292 B2 | 10/2018 | Boudreaux et al. |
| 10,201,364 B2 | 2/2019 | Leimbach et al. |
| 10,231,747 B2 | 3/2019 | Stulen et al. |
| 10,285,724 B2 | 5/2019 | Faller et al. |
| 10,292,701 B2 | 5/2019 | Scheib et al. |
| 10,342,567 B2 | 7/2019 | Hibner et al. |
| 10,368,896 B2 | 8/2019 | Akagane |
| 10,455,052 B2 | 10/2019 | Kimball et al. |
| 10,610,286 B2 | 4/2020 | Wiener et al. |
| 10,687,884 B2 | 6/2020 | Wiener et al. |
| 10,912,580 B2 | 2/2021 | Green et al. |
| 10,945,778 B2 | 3/2021 | Weisenburgh, II et al. |
| 10,945,779 B2 | 3/2021 | Weisenburgh, II et al. |
| 10,966,745 B2 | 4/2021 | Akagane |
| 11,020,140 B2 | 6/2021 | Gee et al. |
| 11,033,322 B2 | 6/2021 | Wiener et al. |
| 11,045,275 B2 | 6/2021 | Boudreaux et al. |
| 11,051,866 B2 | 7/2021 | Estera et al. |
| 11,058,475 B2 | 7/2021 | Wiener et al. |
| 2007/0016236 A1 | 1/2007 | Beaupre |
| 2010/0036405 A1 | 2/2010 | Giordano et al. |
| 2011/0209915 A1 | 9/2011 | Telfort et al. |
| 2012/0116261 A1 | 5/2012 | Mumaw et al. |
| 2014/0135804 A1 | 5/2014 | Weisenburgh, II et al. |
| 2014/0207124 A1 | 7/2014 | Aldridge et al. |
| 2015/0164538 A1 | 6/2015 | Aldridge et al. |
| 2015/0190189 A1 | 7/2015 | Yates et al. |

(56) References Cited

U.S. PATENT DOCUMENTS

| | | | |
|---|---|---|---|
| 2015/0351792 A1* | 12/2015 | Houser | A61B 17/320092 606/171 |
| 2016/0324537 A1* | 11/2016 | Green | A61B 18/1206 |
| 2017/0000516 A1 | 1/2017 | Stulen et al. | |
| 2017/0000541 A1 | 1/2017 | Yates et al. | |
| 2017/0086876 A1 | 3/2017 | Wiener et al. | |
| 2017/0086909 A1 | 3/2017 | Yates et al. | |
| 2018/0333177 A1 | 11/2018 | Leuck et al. | |
| 2018/0333181 A1 | 11/2018 | Lesko et al. | |
| 2018/0333182 A1 | 11/2018 | Clauda | |
| 2018/0333184 A1 | 11/2018 | Leuck et al. | |
| 2018/0333185 A1 | 11/2018 | Asher et al. | |
| 2018/0333186 A1 | 11/2018 | Leuck et al. | |
| 2018/0333187 A1 | 11/2018 | Sawhney | |
| 2018/0333188 A1 | 11/2018 | Nott et al. | |
| 2018/0333189 A1 | 11/2018 | Asher et al. | |
| 2018/0333190 A1 | 11/2018 | Krumm et al. | |
| 2021/0346078 A1 | 11/2021 | Estera | |

FOREIGN PATENT DOCUMENTS

| | | |
|---|---|---|
| CN | 104363843 A | 2/2015 |
| CN | 105286934 A | 2/2016 |
| CN | 105934208 A | 9/2016 |
| CN | 106232038 A | 12/2016 |
| CN | 106413595 A | 2/2017 |
| CN | 106413597 A | 2/2017 |
| CN | 106684603 A | 5/2017 |
| DE | 19905804 C1 | 2/2000 |
| DE | 10 2014 116065 A1 | 5/2016 |
| EP | 0908155 A1 | 4/1999 |
| EP | 2 371 314 A2 | 10/2011 |
| EP | 2 478 861 A2 | 7/2012 |
| EP | 2 641 552 A2 | 9/2013 |
| EP | 3 031 417 A1 | 6/2016 |
| EP | 3 117 790 A1 | 1/2017 |
| EP | 3 287 085 A1 | 2/2018 |
| EP | 2 635 220 B1 | 3/2018 |
| JP | H11-213768 A | 8/1999 |
| JP | 2003-527155 A | 9/2003 |
| JP | 2007-195634 A | 8/2007 |
| JP | 2009-117387 A | 5/2009 |
| JP | 2011-519684 A | 7/2011 |
| JP | 2012-223582 A | 11/2012 |
| JP | 2013-545534 A | 12/2013 |
| JP | 2014-121618 A | 7/2014 |
| JP | 2014-236836 A | 12/2014 |
| JP | 2015-514474 A | 5/2015 |
| JP | 2015-516231 A | 6/2015 |
| JP | 2016-073729 A | 5/2016 |
| WO | WO 1998/037815 A1 | 9/1998 |
| WO | WO 2011/008672 A2 | 1/2011 |
| WO | WO 2012/061645 A1 | 5/2012 |
| WO | 2013/115036 A1 | 8/2013 |
| WO | WO 2015/164193 A1 | 10/2015 |
| WO | WO 2016/091400 A1 | 6/2016 |
| WO | WO 2016/190171 A1 | 12/2016 |
| WO | WO 2017/027853 A1 | 2/2017 |
| WO | WO 2017/058617 A2 | 4/2017 |
| WO | WO 2017/091377 A1 | 6/2017 |
| WO | WO 2017/100427 A2 | 6/2017 |
| WO | WO 2018/093536 A1 | 5/2018 |

OTHER PUBLICATIONS

British Combined Search and Examination Report under Sections 17 and 18(3) dated Aug. 1, 2022, for Application No. 2209985.7, 6 pages.
Chinese Office Action and Search Report dated Aug. 22, 2022, for Application No. 201880033801.4, 9 pages.
Chinese Office Action and Search Report dated Aug. 22, 2022, for Application No. 201880033822.6, 10 pages.
Chinese Office Action and Search Report dated Aug. 23, 2022, for Application No. 201880033501.6, 13 pages.
Chinese Office Action and Search Report dated Aug. 24, 2022, for Application No. 201880034234.4, 12 pages.
Chinese Office Action and Search Report dated Aug. 31, 2022, for Application No. 201880033790.X, 7 pages.
Chinese Office Action and Search Report dated Sep. 5, 2022, for Application No. 201880033752.4, 11 pages.
Chinese Office Action and Search Report dated Sep. 7, 2022, for Application No. 201880033799.0, 14 pages.
European Search Report and Written Opinion dated Apr. 29, 2022, for Application No. 22151018.3, 5 pages.
Japanese Notification of Reasons for Refusal dated May 10, 2022, for Application No. 2019-564433, 6 pages.
Japanese Decision of Refusal dated Nov. 15, 2022, for Application No. 2019-564433, 3 pages.
Japanese Notification of Reasons for Refusal dated Apr. 19, 2022, for Application No. 2019-564468, 5 pages.
Japanese Notification of Reasons for Refusal dated Oct. 25, 2022, for Application No. 2019-564468, 5 pages.
Japanese Notification of Reasons for Refusal dated Apr. 19, 2022, for Application No. 2019-564478, 8 pages.
Japanese Notification of Reasons for Refusal dated Feb. 15, 2022, for Application No. 2019-564481, 6 pages.
Japanese Notification of Reasons for Refusal dated Apr. 19, 2022, for Application No. 2019-564527, 5 pages.
Japanese Notification of Reasons for Refusal dated Nov. 8, 2022, for Application No. 2019-564527, 4 pages.
Japanese Notification of Reasons for Refusal dated Apr. 5, 2022, for Application No. 2019-564528, 5 pages.
Japanese Notification of Reasons for Refusal dated May 10, 2022, for Application No. 2019-564536, 5 pages.
International Search Report and Written Opinion dated Aug. 22, 2018 for Application No. PCT/US2018/033599, 14 pgs.
International Search Report and Written Opinion dated Jan. 2, 2019 for Application No. PCT/US2018/033603, 23 pgs.
International Search Report and Written Opinion dated Nov. 6, 2018 for Application No. PCT/US2018/033605, 14 pgs.
International Search Report and Written Opinion dated Jan. 2, 2019 for Application No. PCT/US2018/033607, 22 pgs.
International Search Report and Written Opinion dated Nov. 6, 2018 for Application No. PCT/US2018/033608, 14 pgs.
International Search Report and Written Opinion dated Sep. 3, 2018 for Application No. PCT/US2018/033615, 13 pgs.
International Search Report and Written Opinion dated Aug. 22, 2018 for Application No. PCT/US2018/033618, 12 pgs.
International Search Report and Written Opinion dated Oct. 19, 2018 for Application No. PCT/US2018/033619, 20 pgs.
U.S. Appl. No. 62/509,351, entitled "Ultrasonic Instrument With Electrosurgical Features," filed May 22, 2017.
British Examination Report under Section 18(3) dated Jan. 17, 2022 for Application No. GB 1919176.6, 2 pgs.
Chinese Office Action, The Second Office Action and Supplementary Search dated Apr. 11, 2023 for Application No. CN 201880033799. 0, 7 pgs.
Chinese Office Action, The Second Office Action, dated May 7, 2023, for Application No. CN 201880033501.6, 10 pages.
Chinese Office Action, The Second Office Action, dated Mar. 15, 2023, for Application No. CN 201880033752.4, 7 pages.
Chinese Office Action, The Third Office Action, dated Jun. 26, 2023, for Application No. CN 201880033752.4, 7 pages.
Chinese Office Action, The Second Office Action, dated Feb. 7, 2023, for Application No. CN 201880034234.4, 4 pages.
Chinese Office Action, The Second Office Action, dated Jun. 3, 2023, for Application No. CN 201880033790.X, 9 pages.
European Search Report and Written Opinion dated Aug. 10, 2021 for Application No. EP 21172089.1, 11 pgs.
European Examination Report dated Feb. 2, 2024 for Application No. EP 22151018.3, 4 pgs.
European Examination Report dated Nov. 28, 2023 for Application No. EP 18731604.7, 7 pgs.
Indian Examination Report dated Feb. 8, 2022 for Application No. IN 201917045572, 6 pgs.

(56) References Cited

OTHER PUBLICATIONS

Indian Examination Report dated Feb. 8, 2022 for Application No. IN 201917045284, 7 pgs.
Indian Examination Report dated Mar. 7, 2022 for Application No. IN 201917045576, 5 pgs.
Indian Examination Report dated Jan. 10, 2024 for Application No. IN 201917045574, 8 pgs.
Indian Examination Report dated Feb. 11, 2022 for Application No. IN 201917045570, 7 pgs.
Indian Examination Report dated Feb. 16, 2022 for Application No. IN 201917045832, 6 pgs.
Indian Examination Report dated Feb. 25, 2022 for Application No. IN 201917045836, 7 pgs.
Indian Examination Report dated Feb. 7, 2022 for Application No. IN 201917045834, 5 pgs.
Japanese Search Report by Registered Search Organization, dated Mar. 18, 2022 for Application No. JP 2019-564478, 29 pgs.
Japanese Office Action, Notice of Reasons for Refusal, dated May 10, 2022 for Application No. JP 2019-564432, 8 pgs.
Japanese Search Report by Registered Search Organization, dated Mar. 18, 2022 for Application No. JP 2019-564432, 19 pgs.
Japanese Office Action, Decision of Refusal, dated Nov. 15, 2022 for Application No. JP 2019-564432, 6 pgs.

* cited by examiner

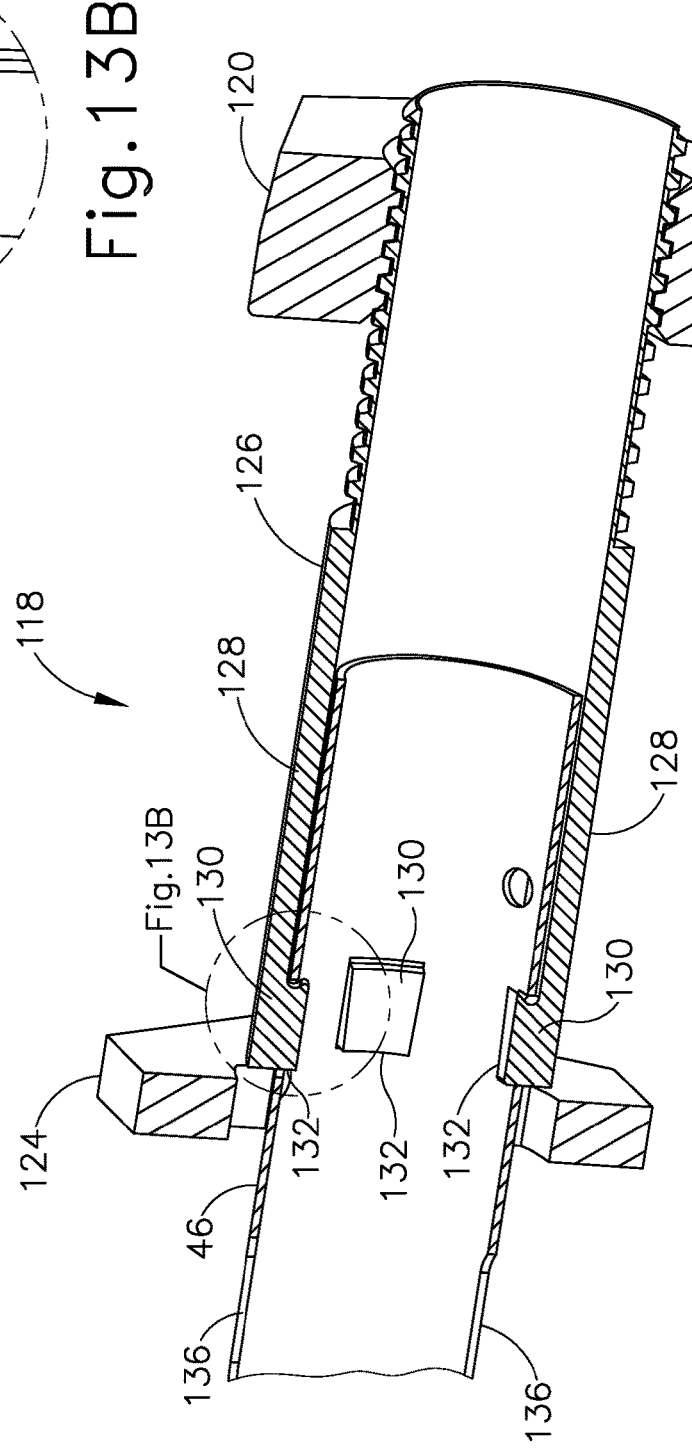
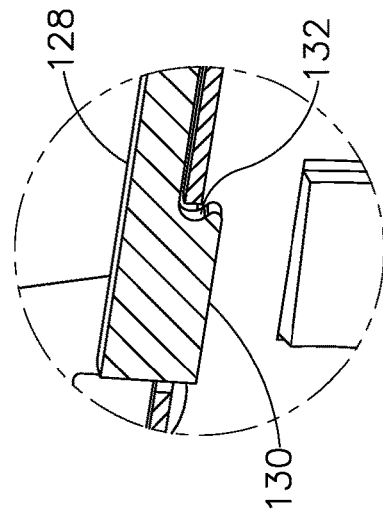
Fig.13A
Fig.13B

ABSTRACT# COMBINATION ULTRASONIC AND ELECTROSURGICAL INSTRUMENT HAVING ELECTRICAL CIRCUITS WITH SHARED RETURN PATH

This application is a continuation of U.S. patent application Ser. No. 15/967,740, entitled Ultrasonic Instrument With Electrosurgical Features," filed May 1, 2018 and published as U.S. Pat. Pub. No. 2018/0333177, now issued as U.S. Pat. No. 11,234,750 on Feb. 1, 2022, now U.S. Pat. No. 11,234,750, which claims the benefit of U.S. Provisional App. No. 62/509,351, entitled "Ultrasonic Instrument With Electrosurgical Features," filed May 22, 2017, the disclosure of which is incorporated by reference herein.

BACKGROUND

Ultrasonic surgical instruments utilize ultrasonic energy for both precise cutting and controlled coagulation of tissue. The ultrasonic energy cuts and coagulates by vibrating a blade in contact with the tissue. Vibrating at frequencies of approximately 50 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVER Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,095,367, entitled "Flexible Harmonic Waveguides/Blades for Surgical Instruments," issued Aug. 4, 2015, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017, the disclosure of which is incorporated by reference herein.

Electrosurgical instruments utilize electrical energy for sealing tissue, and generally include a distally mounted end effector that can be configured for bipolar or monopolar operation. During bipolar operation, electrical current is provided through the tissue by active and return electrodes of the end effector. During monopolar operation, current is provided through the tissue by an active electrode of the end effector and a return electrode (e.g., a grounding pad) separately located on a patient's body. Heat generated by the current flowing through the tissue may form hemostatic seals within the tissue and/or between tissues, and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator coupled with the instrument. The electrical energy may be in the form of radio frequency ("RF") energy, which is a form of electrical energy generally in the frequency range of approximately 300 kilohertz (kHz) to 1 megahertz (MHz). In use, an electrosurgical device can transmit lower frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy works particularly well on connective tissue, which is primarily comprised of collagen and shrinks when contacted by heat.

An example of an RF electrosurgical device is the ENSEAL® Tissue Sealing Device by Ethicon Endo-Surgery, Inc., of Cincinnati, Ohio. Further examples of electrosurgical devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical devices and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; U.S. Pat. No. 9,545,253, entitled "Surgical Instrument with Contained Dual Helix Actuator Assembly," issued Jan. 17, 2017, the disclosure of which is incorporated by reference herein; and U.S. Pat. No. 9,572,622, entitled "Bipolar Electrosurgical Features for Targeted Hemostasis," issued Feb. 21, 2017, the disclosure of which is incorporated by reference herein.

Some instruments may provide ultrasonic and RF energy treatment capabilities through a single surgical device. Examples of such devices and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, issued as U.S. Pat. No. 11,141,213 on Oct. 12, 2021, the disclosure of which is incorporated by reference herein.

While various types of ultrasonic surgical instruments and electrosurgical instruments, including combination ultrasonic-electrosurgical instruments, have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 13A depicts a sectional perspective view of the spring retainer and outer tube of FIG. 12;

FIG. 13B depicts an enlarged sectional perspective view of a region indicated in FIG. 13A, showing features that provide a snap-fit engagement between the spring retainer and the outer tube;

Figure 1:
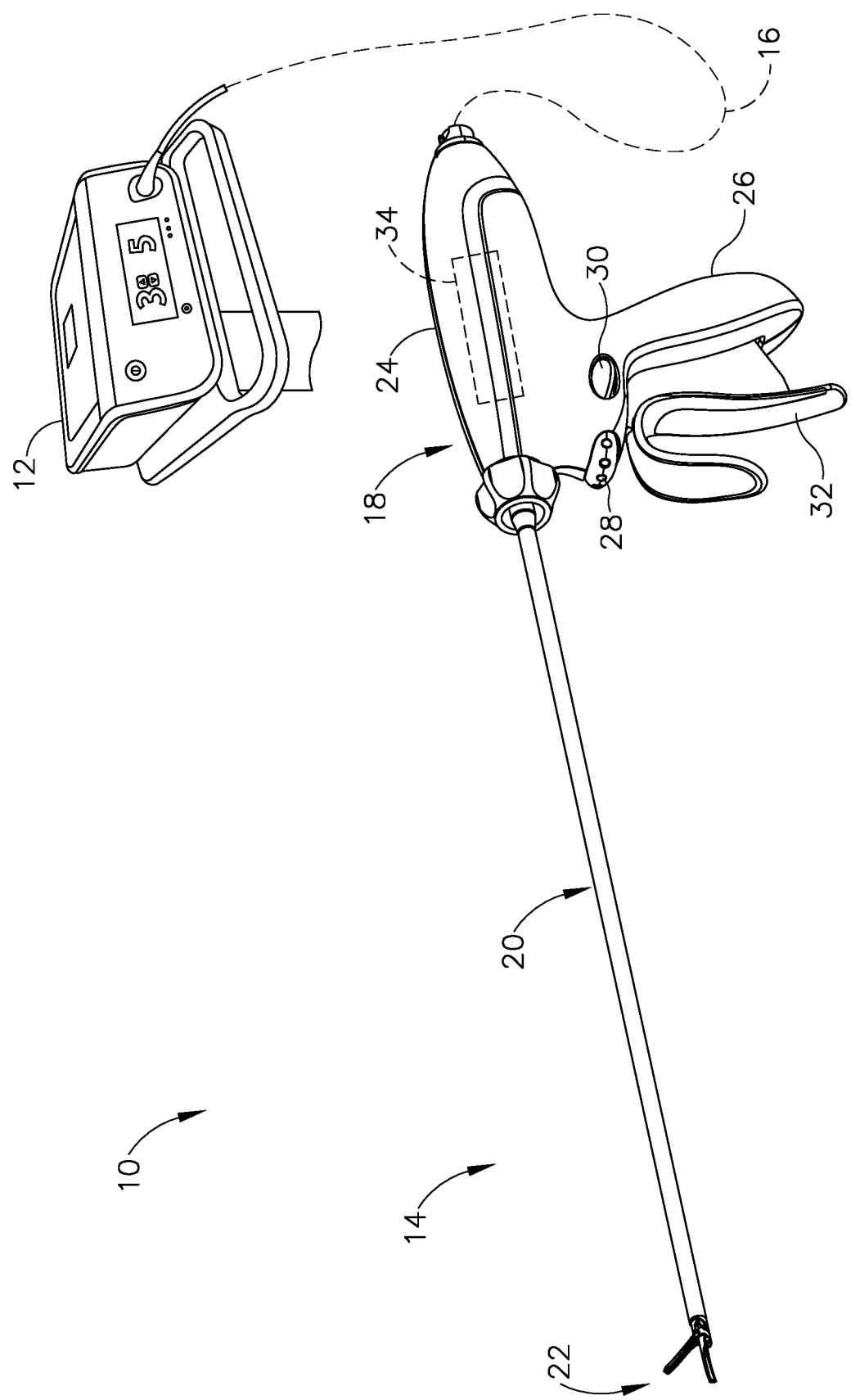
FIG. 1 depicts a perspective view of an exemplary surgical system having a generator and a surgical instrument operable to treat tissue with ultrasonic energy and bipolar RF energy.

The drawings are not intended to be limiting in any way, and it is contemplated that various embodiments of the invention may be carried out in a variety of other ways, including those not necessarily depicted in the drawings.

The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Exemplary Surgical System

FIG. 1 depicts an exemplary surgical system (10) including a generator (12) and a surgical instrument (14). Surgical instrument (14) is operatively coupled with the generator (12) via power cable (16). As described in greater detail below, generator (12) is operable to power surgical instrument (14) to deliver ultrasonic energy for cutting tissue, and electrosurgical bipolar RF energy (i.e., therapeutic levels of RF energy) for sealing tissue. In exemplary configurations, generator (12) is configured to power surgical instrument (14) to deliver ultrasonic energy and electrosurgical bipolar RF energy simultaneously.

A. Overview of Exemplary Surgical Instrument with Ultrasonic and Electrosurgical Features Surgical instrument (14) of the present example comprises a handle assembly (18), a shaft assembly (20) extending distally from the handle assembly (18), and an end effector (22) arranged at a distal end of the shaft assembly (20). Handle assembly (18) comprises a body (24) including a pistol grip (26) and energy control buttons (28, 30) configured to be manipulated by a surgeon. A trigger (32) is coupled to a lower portion of body (24) and is pivotable toward and away from pistol grip (26) to selectively actuate end effector (22), as described in greater detail below. In other suitable variations of surgical instrument (14), handle assembly (18) may comprise a scissor grip configuration, for example. As described in greater detail below, an ultrasonic transducer (34) is housed internally within and supported by body (24). In other configurations, ultrasonic transducer (34) may be provided externally of body (24).

Figure 2:
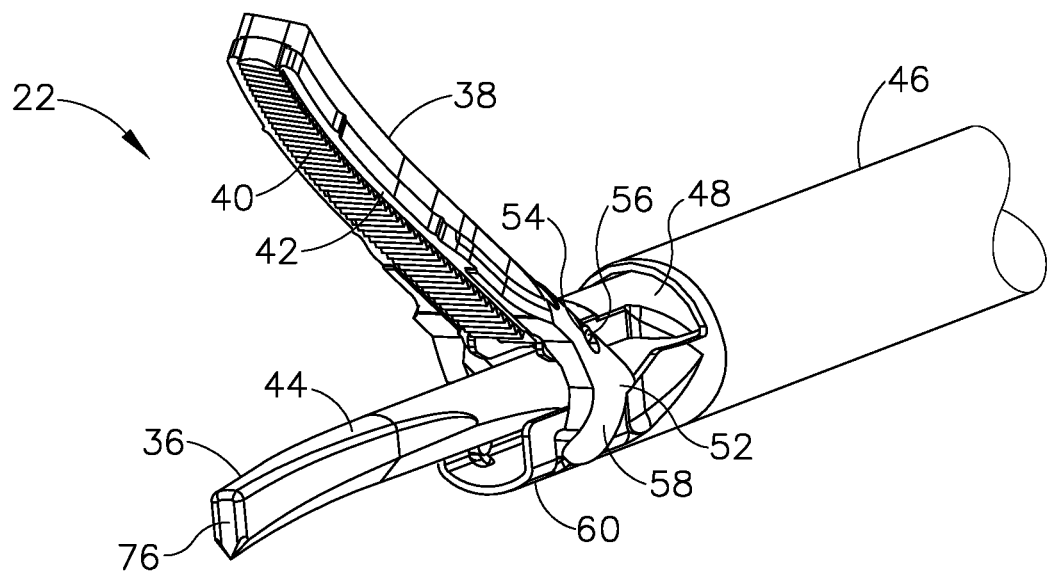
FIG. 2 depicts a top perspective view of an end effector of the surgical instrument of FIG. 1, having a clamp arm that provides a first electrode and an ultrasonic blade that provides a second electrode.
Figure 3:
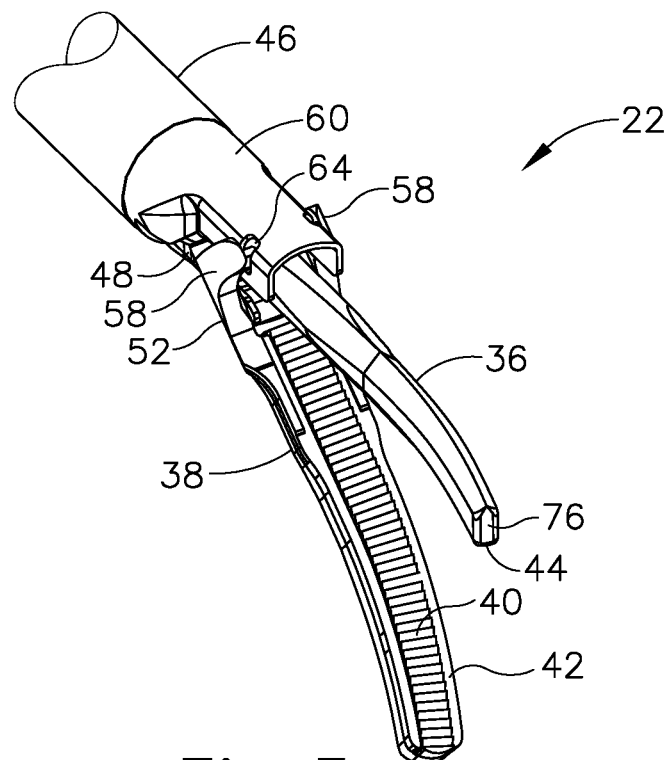
FIG. 3 depicts a bottom perspective view of the end effector of FIG. 2.

As shown in FIGS. 2 and 3, end effector (22) includes an ultrasonic blade (36) and a clamp arm (38) configured to selectively pivot toward and away from ultrasonic blade (36), for clamping tissue therebetween. Ultrasonic blade (36) is acoustically coupled with ultrasonic transducer (34), which is configured to drive (i.e., vibrate) ultrasonic blade (36) at ultrasonic frequencies for cutting and/or sealing tissue positioned in contact with ultrasonic blade (36). Clamp arm (38) is operatively coupled with trigger (32) such that clamp arm (38) is configured to pivot toward ultrasonic blade (36), to a closed position, in response to pivoting of trigger (32) toward pistol grip (26). Further, clamp arm (38) is configured to pivot away from ultrasonic blade (36), to an open position (see e.g., FIGS. 1-3), in response to pivoting of trigger (32) away from pistol grip (26). Various suitable ways in which clamp arm (38) may be coupled with trigger (32) will be apparent to those of ordinary skill in the art in view of the teachings provided herein. In some versions, one or more resilient members may be incorporated to bias clamp arm (38) and/or trigger (32) toward the open position.

A clamp pad (40) is secured to and extends distally along a clamping side of clamp arm (38), facing ultrasonic blade (36). Clamp pad (40) is configured to engage and clamp tissue against a corresponding tissue treatment portion of ultrasonic blade (36) when clamp arm (38) is actuated to its closed position. At least a clamping-side of clamp arm (38) provides a first electrode (42), referred to herein as clamp arm electrode (42). Additionally, at least a clamping-side of ultrasonic blade (36) provides a second electrode (44), referred to herein as a blade electrode (44). As described in greater detail below, electrodes (42, 44) are configured to apply electrosurgical bipolar RF energy, provided by generator (12), to tissue electrically coupled with electrodes (42, 44). Clamp arm electrode (42) may serve as an active electrode while blade electrode (44) serves as a return electrode, or vice-versa. Surgical instrument (14) may be configured to apply the electrosurgical bipolar RF energy through electrodes (42, 44) while vibrating ultrasonic blade (36) at an ultrasonic frequency, before vibrating ultrasonic blade (36) at an ultrasonic frequency, and/or after vibrating ultrasonic blade (36) at an ultrasonic frequency.

As shown in FIGS. 1-5, shaft assembly (20) extends along a longitudinal axis and includes an outer tube (46), an inner tube (48) received within outer tube (46), and an ultrasonic waveguide (50) supported within inner tube (48). As seen best in FIGS. 2-5, clamp arm (38) is coupled to distal ends of inner and outer tubes (46, 48). In particular, clamp arm (38) includes a pair of proximally extending clevis arms (52) that receive therebetween and pivotably couple to a distal end (54) of inner tube (48) with a pivot pin (56) received within through bores formed in clevis arms (52) and distal end (54) of inner tube (48). First and second clevis fingers (58) depend downwardly from clevis arms (52) and pivotably couple to a distal end (60) of outer tube (46). Specifically, each clevis finger (58) includes a protrusion (62) that is rotatably received within a corresponding opening (64) formed in a sidewall of distal end (60) of outer tube (46).

In the present example, inner tube (48) is longitudinally fixed relative to handle assembly (18), and outer tube (46) is configured to translate relative to inner tube (48) and handle assembly (18), along the longitudinal axis of shaft assembly (20). As outer tube (46) translates distally, clamp arm (38) pivots about pivot pin (56) toward its open position. As outer tube (46) translates proximally, clamp arm (38) pivots in an opposite direction toward its closed position. As described below with reference to FIG. 11, a proximal end of outer tube (46) is operatively coupled with trigger (32), for example via a linkage assembly, such that actuation of trigger (32) causes translation of outer tube (46) relative to inner tube (48), thereby opening or closing clamp arm (38). In other suitable configurations not shown herein, outer tube (46) may be longitudinally fixed and inner tube (48) may be configured to translate for moving clamp arm (38) between its open and closed positions.

Shaft assembly (20) and end effector (22) are configured to rotate together about the longitudinal axis, relative to handle assembly (18). A retaining pin (66), shown in FIG. 4, extends transversely through proximal portions of outer tube (46), inner tube (48), and waveguide (50) to thereby couple these components rotationally relative to one another. In the present example, a rotation knob (68) is provided at a proximal end portion of shaft assembly (20) to facilitate rotation of shaft assembly (20), and end effector (22), relative to handle assembly (18). Rotation knob (68) is secured rotationally to shaft assembly (20) with retaining pin (66), which extends through a proximal collar of rotation knob (68). It will be appreciated that in other suitable configurations, rotation knob (68) may be omitted or substituted with alternative rotational actuation structures.

Figure 5:
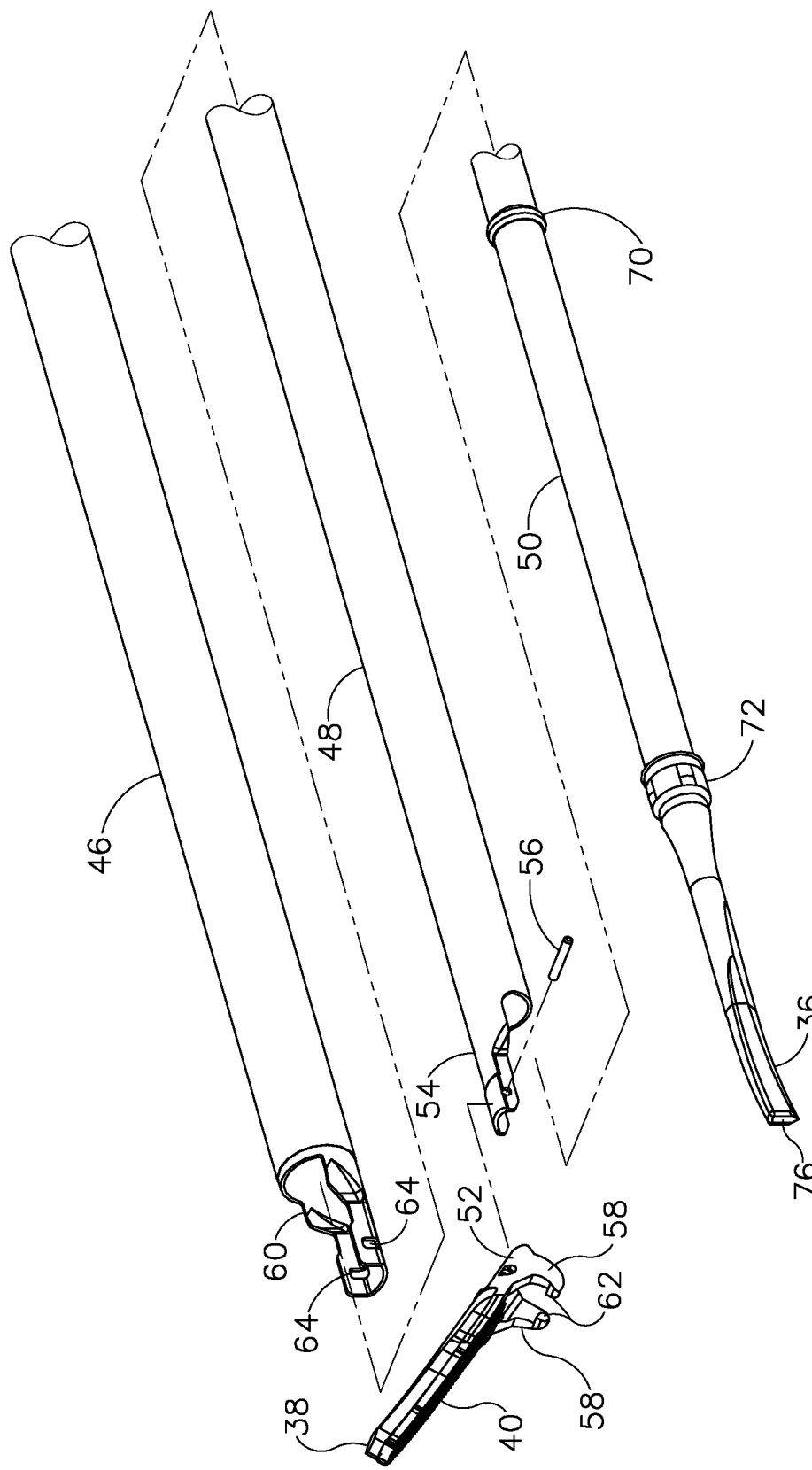
FIG. 5 depicts an enlarged exploded perspective view of a distal portion of the shaft assembly and the end effector of the surgical instrument of FIG. 1.

Ultrasonic waveguide (50) is acoustically coupled at its proximal end with ultrasonic transducer (34), for example by a threaded connection, and at its distal end with ultrasonic blade (36), as shown in FIG. 5. Ultrasonic blade (36) is shown formed integrally with waveguide (50) such that blade (36) extends distally, directly from the distal end of waveguide (50). In this manner, waveguide (50) acoustically couples ultrasonic transducer (34) with ultrasonic blade (36), and functions to communicate ultrasonic mechanical vibrations from transducer (34) to blade (36). Accordingly, ultrasonic transducer (34), waveguide (50), and ultrasonic blade (36) together define acoustic assembly (100). During use, ultrasonic blade (36) may be positioned in direct contact with tissue, with or without assistive clamping force provided by clamp arm (38), to impart ultrasonic vibrational energy to the tissue and thereby cut and/or seal the tissue. For example, blade (36) may cut through tissue clamped between clamp arm (38) and a first treatment side of blade (36), or blade (36) may cut through tissue positioned in contact with an oppositely disposed second treatment side of blade (36), for example during a "back-cutting" movement. In some variations, waveguide (50) may amplify the ultrasonic vibrations delivered to blade (36). Further, waveguide (50) may include various features operable to control the gain of the vibrations, and/or features suitable to tune waveguide (50) to a selected resonant frequency. Additional exemplary features of ultrasonic blade (36) and waveguide (50) are described in greater detail below.

Figure 4:
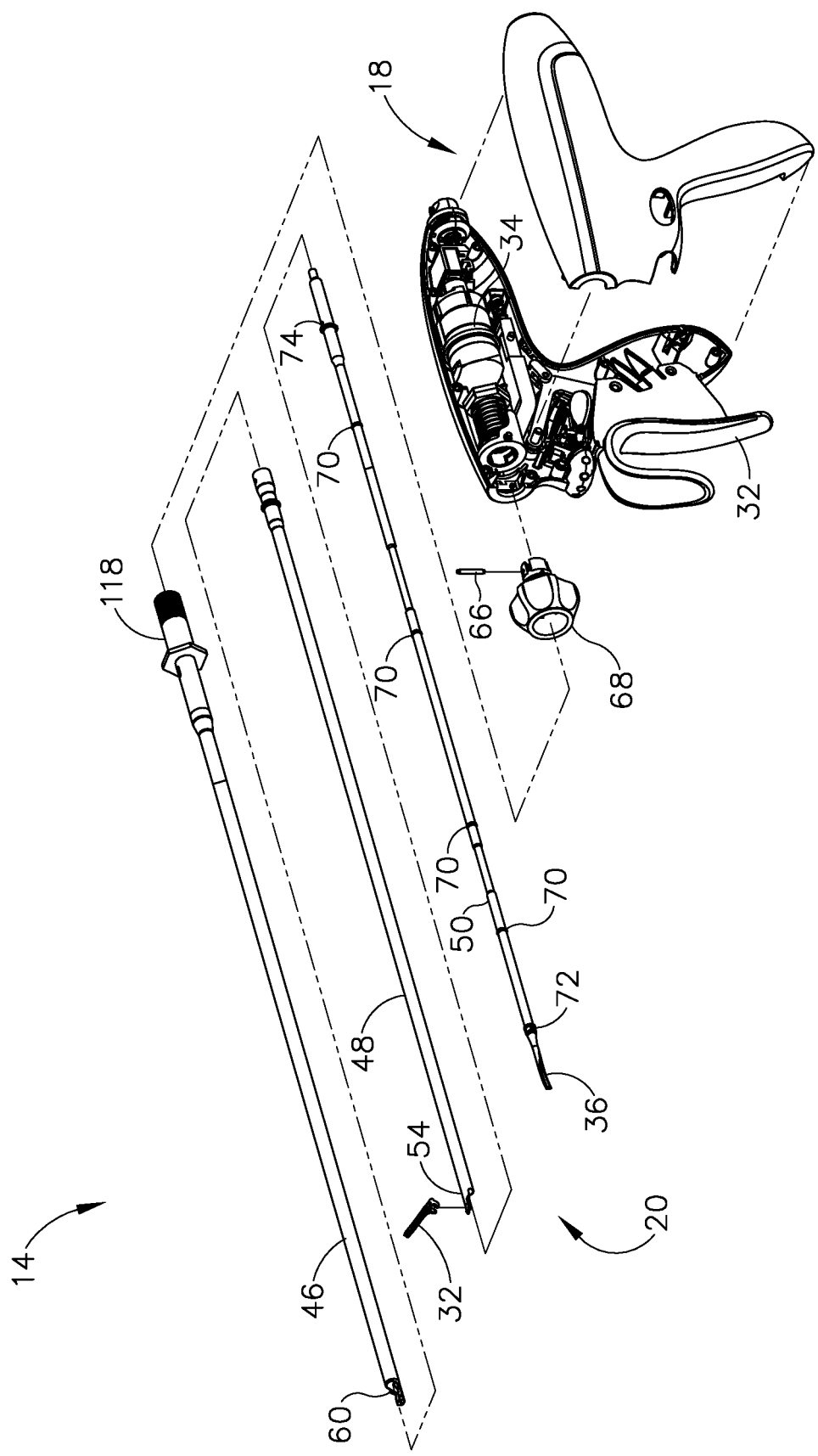
FIG. 4 depicts a partially exploded perspective view of the surgical instrument of FIG. 1.

Waveguide (50) is supported within inner tube (48) by a plurality of nodal support elements (70) positioned along a length of waveguide (50), as shown in FIGS. 4 and 5. Specifically, nodal support elements (70) are positioned longitudinally along waveguide (50) at locations corresponding to acoustic nodes defined by the resonant ultrasonic vibrations communicated through waveguide (50). Nodal support elements (70) may provide structural support to waveguide (50), and acoustic isolation between waveguide (50) and inner and outer tubes (46, 48) of shaft assembly (20). In exemplary variations, nodal support elements (70) may comprise o-rings. Waveguide (50) is supported at its distal-most acoustic node by a nodal support element in the form of an overmold member (72), shown in FIG. 5. Waveguide (50) is secured longitudinally and rotationally within shaft assembly (20) by retaining pin (66), which passes through a transverse through-bore (74) formed at a proximally arranged acoustic node of waveguide (50), such as the proximal-most acoustic node, for example.

In the present example, a distal tip (76) of ultrasonic blade (36) is located at a position corresponding to an anti-node associated with the resonant ultrasonic vibrations communicated through waveguide (50). Such a configuration enables the acoustic assembly (100) of instrument (14) to be tuned to a preferred resonant frequency $f_0$ when ultrasonic blade (36) is not loaded by tissue. When ultrasonic transducer (34) is energized by generator (12) to transmit mechanical vibrations through waveguide (50) to blade (36), distal tip (76) of blade (36) is caused to oscillate longitudinally in the range of approximately 20 to 120 microns peak-to-peak, for example, and in some instances in the range of approximately 20 to 50 microns, at a predetermined vibratory frequency $f_0$ of approximately 50 kHz, for example. When ultrasonic blade (36) is positioned in contact with tissue, the ultrasonic oscillation of blade (36) may simultaneously sever the tissue and denature the proteins in adjacent tissue cells, thereby providing a coagulative effect with minimal thermal spread.

Figure 6:
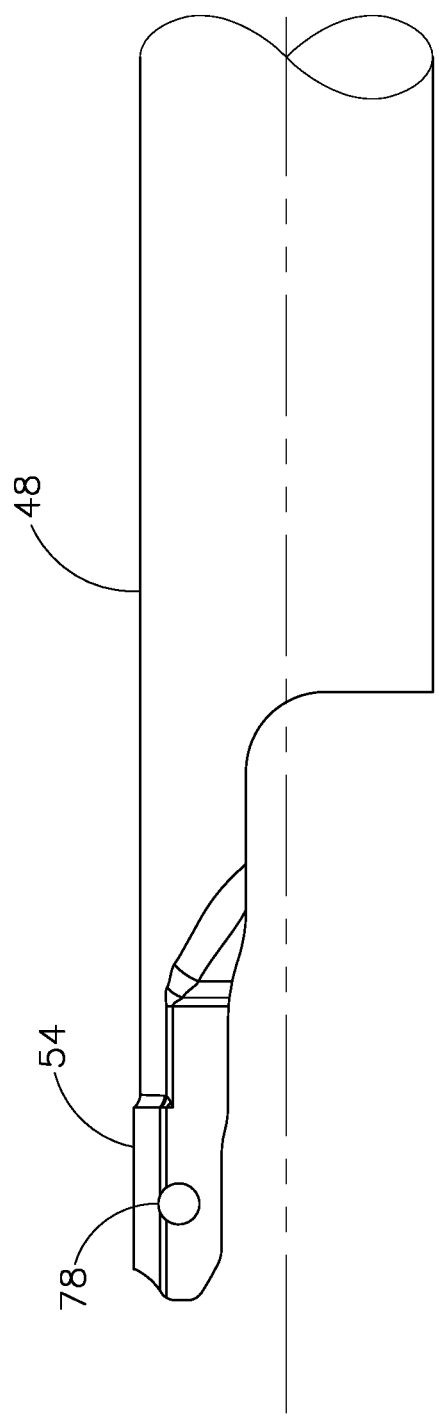
FIG. 6 depicts a side elevational view of a distal portion of an inner tube of the shaft assembly of the surgical instrument of FIG. 1.
Figure 7:
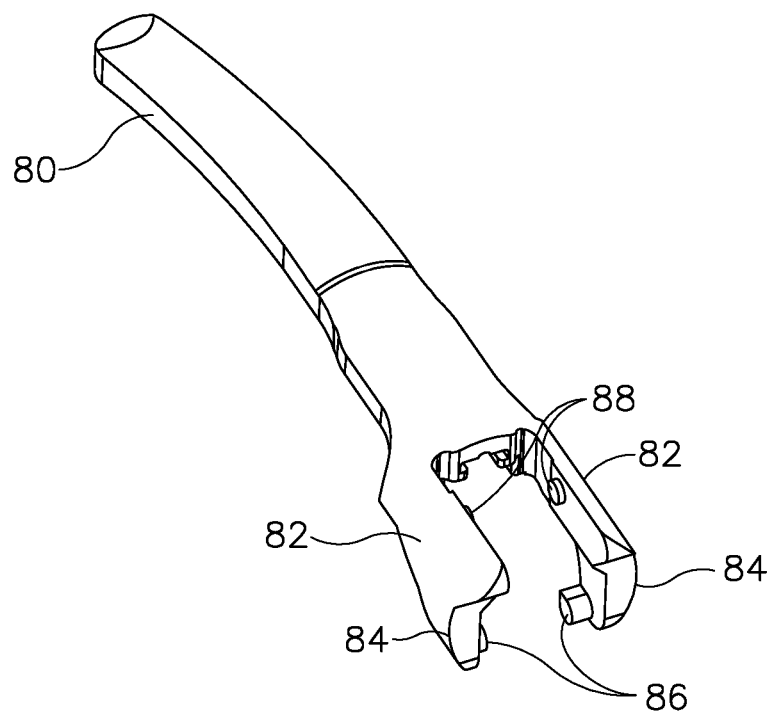
FIG. 7 depicts a rear perspective view of another exemplary clamp arm configured for use with the surgical instrument of FIG. 1, the clamp arm having integrally formed pivot pins.
Figure 8:
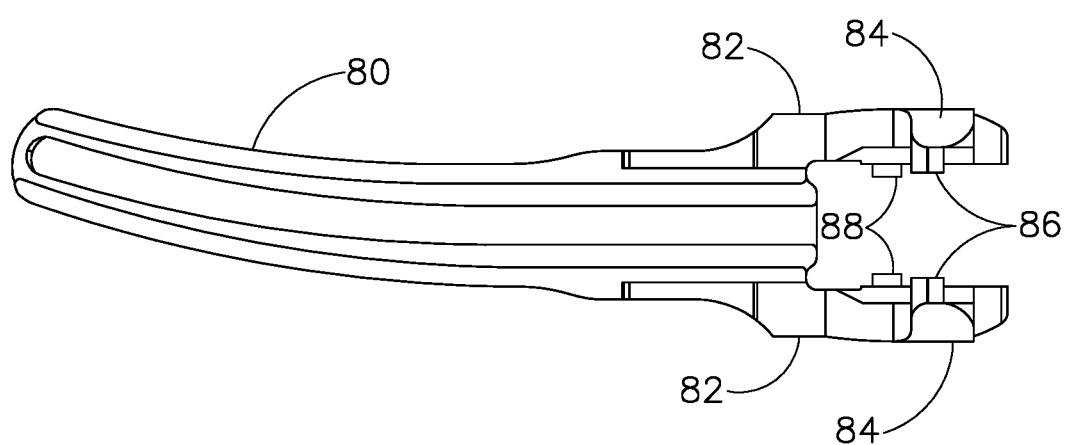
FIG. 8 depicts a bottom elevational view of the clamp arm of FIG. 7.

As shown in FIG. 6, distal end (54) of inner tube (48) may be offset radially outwardly relative to a remaining proximal portion of inner tube (48). This configuration enables pivot pin bore (78), which receives clamp arm pivot pin (56), to be spaced further away from the longitudinal axis of shaft assembly (20) than if distal end (54) where formed flush with the remaining proximal portion of inner tube (48). Advantageously, this provides increased clearance between proximal portions of clamp arm electrode (42) and blade electrode (44), thereby mitigating risk of undesired "shorting" between electrodes (42, 44) and their corresponding active and return electrical paths, for example during back-cutting when ultrasonic blade (36) flexes toward clamp arm (38) and pivot pin (56) in response to normal force exerted on blade (36) by tissue. In other words, when ultrasonic blade (36) is used in a back-cutting operation, ultrasonic blade (36) may tend to deflect slightly away from the longitudinal axis of shaft assembly (20), toward pin (56). By having pivot pin bore (78) spaced further away from the longitudinal axis than pivot pin bore (78) otherwise would be in the absence of the radial offset provided by distal end (54) of the present example, distal end (54) provides additional lateral clearance between pivot pin (56) and ultrasonic blade (36), thereby reducing or eliminating the risk of contact between ultrasonic blade (36) and pivot pin (56) when ultrasonic blade (36) deflects laterally during back-cutting operations. In addition to preventing electrical short circuits that would otherwise result from contact between ultrasonic blade (36) and pivot pin (56) when end effector (22) is activated to apply RF electrosurgical energy, the additional clearance prevents mechanical damage that might otherwise result from contact between ultrasonic blade (36) and pivot pin (56) when ultrasonic blade (36) is vibrating ultrasonically.

B. Exemplary Alternative Clamp Arm with Integral Pivot Pins

FIGS. 7-10 show another exemplary clamp arm (80) configured for use with surgical instrument (14). Similar to clamp arm (38), clamp arm (80) includes a pair of proximally extending clevis arms (82) and a pair of clevis fingers (84) depending downwardly from clevis arms (82) and including protrusions (86). Clevis arms (82) are configured to receive therebetween and pivotably couple to distal end (54) of inner tube (48). However, rather than including through-bores configured to receive pivot pin (56), clevis arms (82) includes a pair of integrally formed pivot pins (88)

projecting inwardly from inner faces of clevis arms (82). Integral pivot pins (88) are configured to be rotatably received within pivot pin bore (78) of inner tube (48), with a snap-fit engagement. Accordingly, clamp arm (80) includes a fist set of integral pivoting elements, in the form of protrusions (86), that pivotably couple clamp arm (80) to distal end (60) of outer tube (46); and a second set of integral pivoting elements, in the form of integral pivot pins (88), that pivotably couple clamp arm (80) to distal end (54) of inner tube (48).

Figure 9:
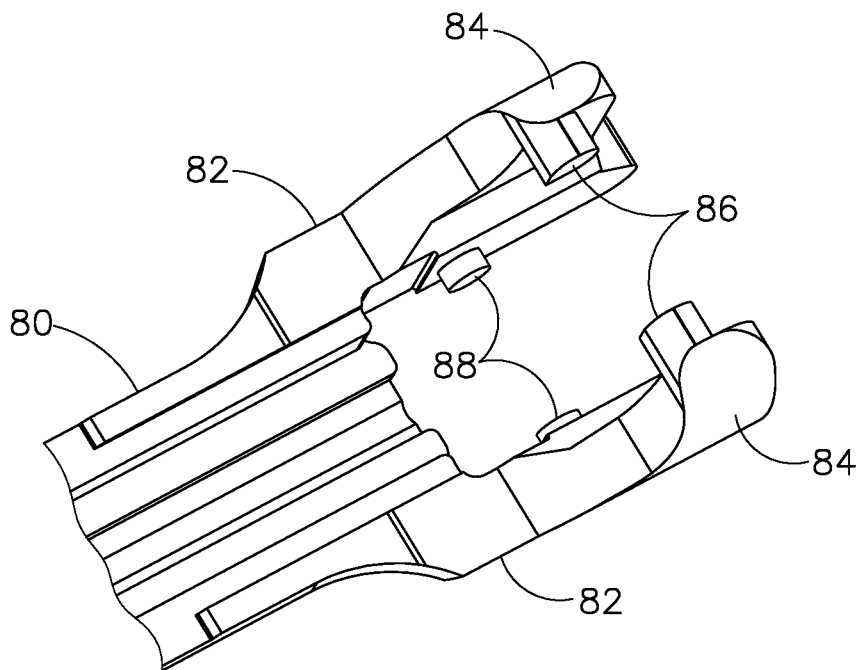
FIG. 9 depicts bottom perspective view of a proximal portion of the clamp arm of FIG. 7.
Figure 10:
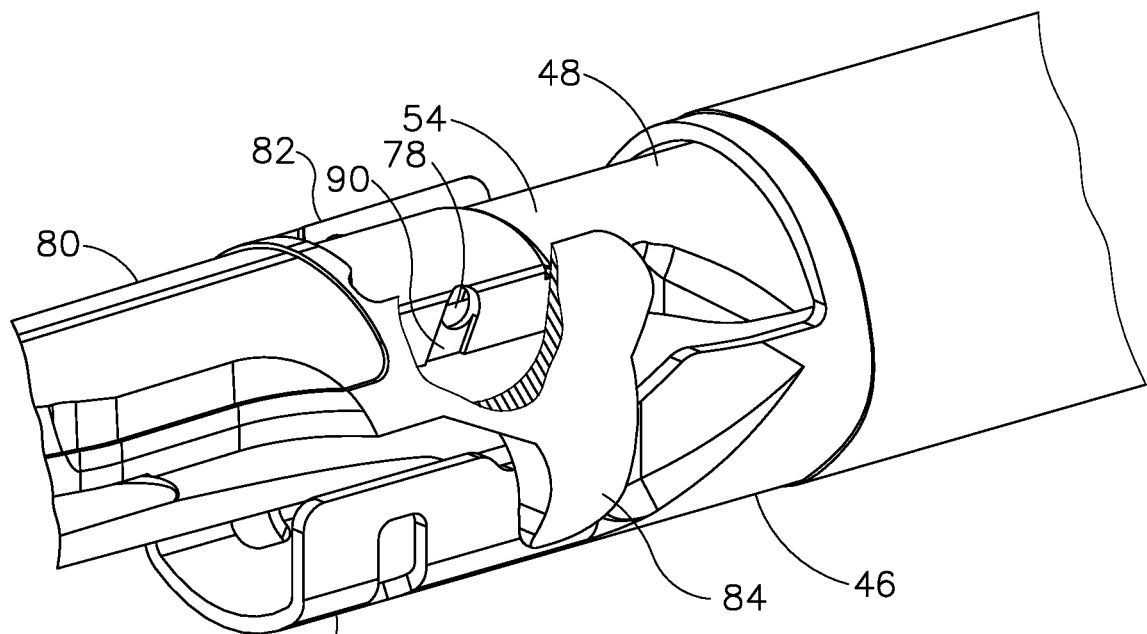
FIG. 10 depicts a perspective view of the clamp arm of FIG. 7 coupled to the distal end of an inner tube of the surgical instrument of FIG. 1, the inner tube modified to include a groove that guides the integral pivot pins.

As shown in FIG. 9, integral pivot pins (88) may include rounded or chamfered edges to facilitate coupling of clamp arm (80) to inner tube (48) during assembly. As shown in FIG. 10, distal end (54) of inner tube (48) may include a lead-in groove (90) extending transversely into each opening of pivot pin bore (78). Advantageously, lead-in groove (90) may guide integral pivot pins (88) into pivot pin bore (78) during snap-fit assembly of clamp arm (80) with inner tube (48).

In versions where clamp arm includes integral pivot pins (88), pivot pin (56) would be omitted. Thus, the above-described risks associated with contact between ultrasonic blade (36) and pivot pin (56) would be avoided. In other words, the configuration of integral pivot pins (88) would allow end effector (22) to accommodate substantial lateral deflection of ultrasonic blade (36) during back-cutting operations, since a portion of the laterally deflected ultrasonic blade (36) could be received in the gap defined between integral pivot pins (88).

C. Exemplary Handle and Shaft Assemblies

Figure 11:
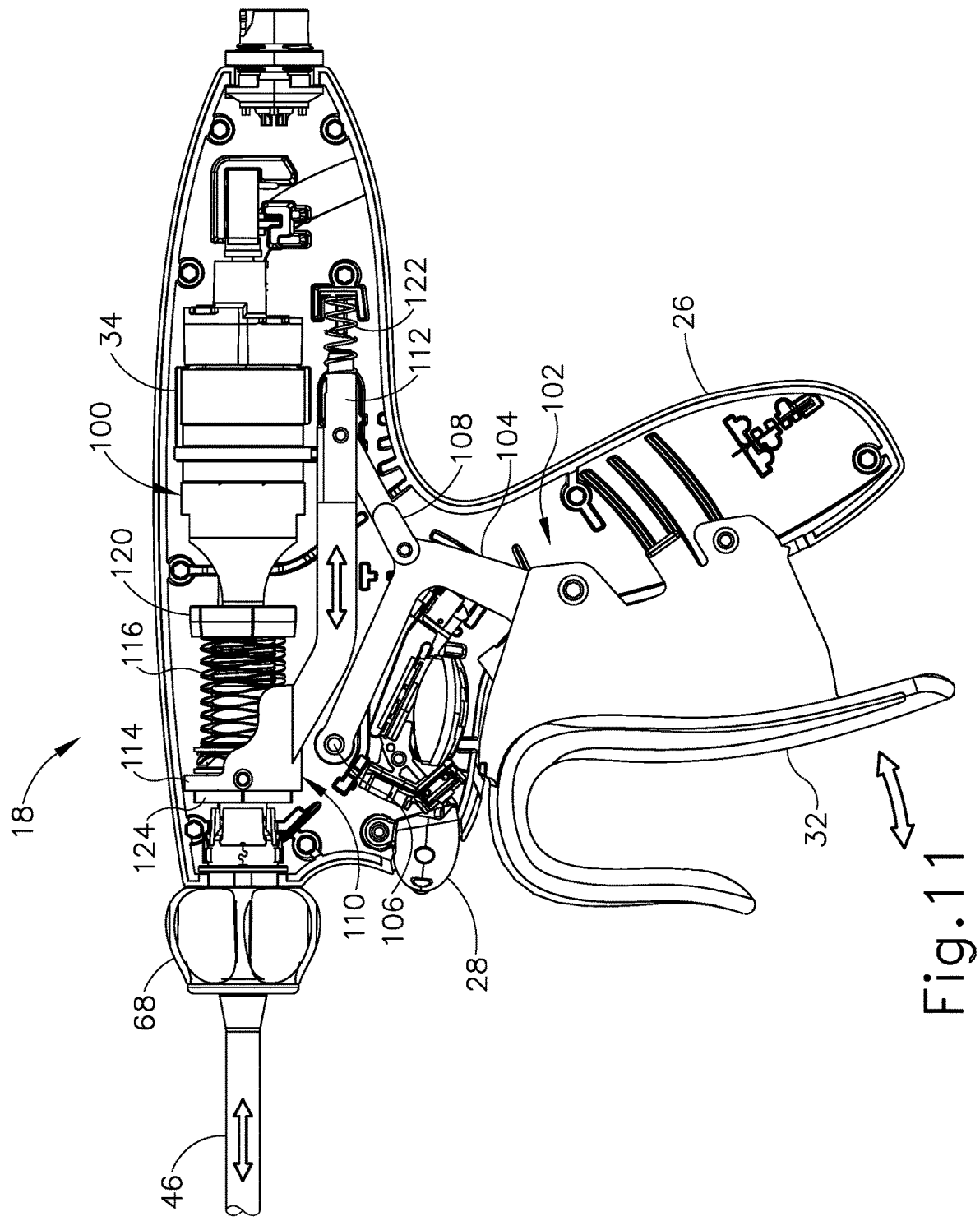
FIG. 11 depicts a side elevational view of a handle assembly of the surgical instrument of FIG. 1, with a side portion of the body of the handle assembly omitted to expose internal components, including an actuation assembly having a trigger and an acoustic assembly having an ultrasonic transducer.

FIG. 11 shows additional details of features housed within handle assembly (18) of surgical instrument (14), including an acoustic assembly (100) and an actuation assembly (102). Acoustic assembly (100) is described in greater detail below with reference to FIG. 15A. Actuation assembly (102) includes trigger (32) and a series of links that operatively couple trigger (32) with outer tube (46) and thus clamp arm (38), such that pivoting of trigger (32) relative to body (24) may cause pivoting of clamp arm (38) relative to ultrasonic blade (36). More specifically, trigger (32) is coupled to a first link (104) that pivots about pivot point (106). First link (104) is pivotably coupled at a medial elbow portion thereof to a distal end of a second link (108). Second link (108) is pivotably at its proximal end to a proximal arm (112) of a translating member (110). Arm (112) is rigidly connected at its distal end to a yoke (114) of translating member (110). Yoke (114) at least partially encircles and operatively couples with a proximal end of outer tube (46). In particular, yoke (114) abuts a distal end of a spring stack (116) that is retained on a cylindrical spring retainer (118) (see FIG. 12) by a proximal retaining nut (120), as described in greater detail below with reference to FIGS. 12-13B. Spring stack (116) comprises a linearly arranged array of adjacent wave springs in this example. Spring retainer (118) fixedly couples to a proximal end of outer tube (46).

As indicated by directional arrows in FIG. 11, squeezing trigger (32) toward pistol grip (26) actuates outer tube (46) proximally to thereby close clamp arm (38), and releasing trigger (32) enables outer tube to actuate distally to thereby open clamp arm (38). In particular, moving trigger (32) toward pistol grip (26) (e.g., by squeezing) causes first and second links (104, 108) to pivot about their respective pivot axes and drive translating member (110) proximally along the longitudinal axis of shaft assembly (20). Proximal movement of translating member (110) causes yoke (114) to compress spring stack (116) proximally against retaining nut (120), which drives spring retainer (118) and outer tube (46) proximally. As described above, proximal translation of outer tube (46) causes clamp arm (38) to pivot toward its closed position.

In the present example, actuation assembly (102) further includes a compression spring (122) arranged at a proximal end of arm (112) of translating member (110), and which biases translating member (110) distally. When trigger (32) is released, compression spring (122) drives translating member distally so that yoke (114) engages a distal flange (124) of spring retainer (118). Because spring retainer (118) is fixed to outer tube (46), yoke (114) drives spring retainer and outer tube (46) distally together, which causes clamp arm (38) to return to its open position.

Though not shown herein, it will be appreciated that actuation assembly (102) may be supplemented or substituted with a motor assembly configured to provide powered actuation of clamp arm (38). Exemplary surgical devices incorporating motor assemblies are disclosed in U.S. Pat. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein; U.S. Pat. Pub. No. 2015/0374360, entitled "Articulation Drive Features for Surgical Stapler," published Dec. 31, 2015, issued as U.S. Pat. No. 10,292,701 on May 21, 2019, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, incorporated by reference above; and U.S. Pat. No. 9,161,803, entitled "Motor Driven Electrosurgical Device with Mechanical and Electrical Feedback," issued Oct. 20, 2015, incorporated by reference above.

Figure 12:
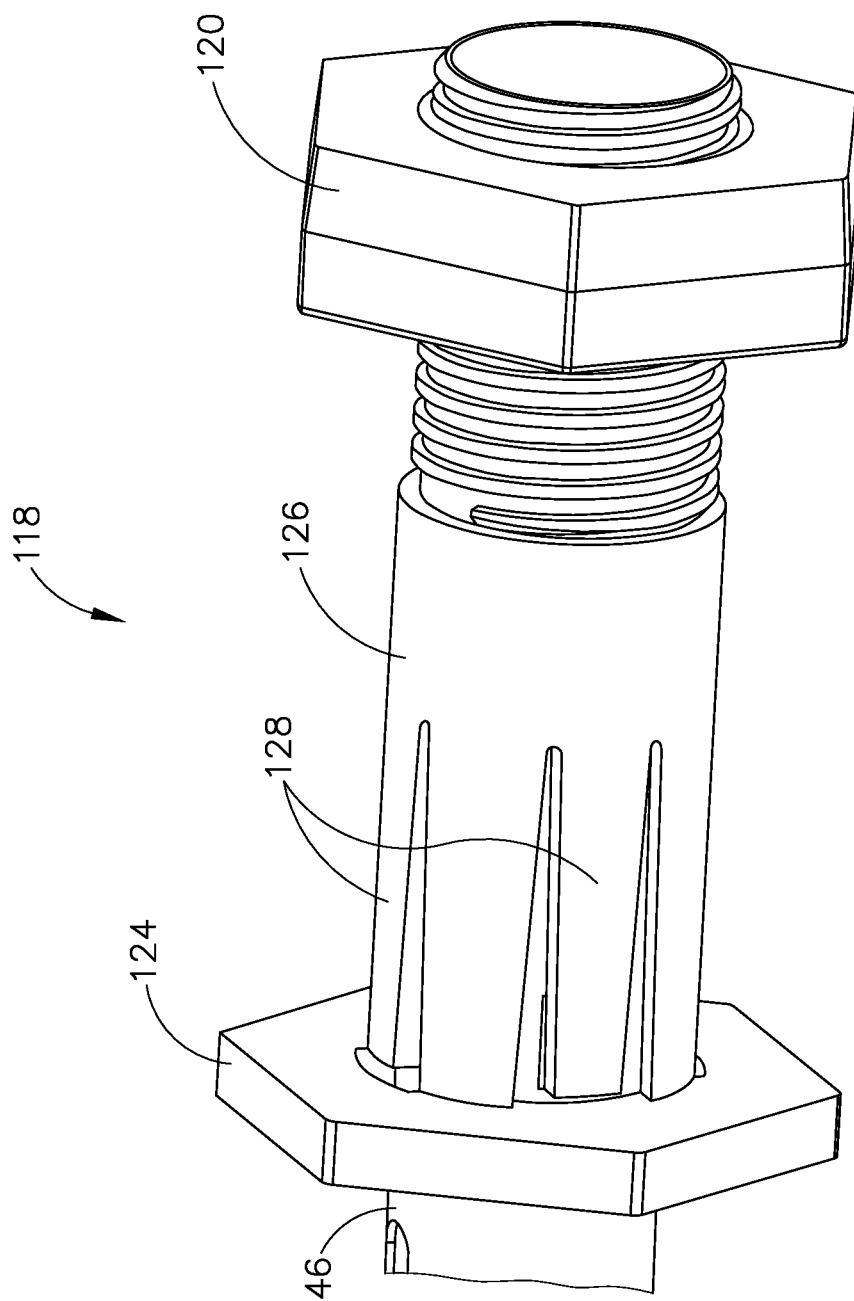
FIG. 12 depicts a perspective view of a spring retainer coupled to a proximal end of the outer tube of the surgical instrument of FIG. 11.

FIGS. 12-13B show additional details of spring retainer (118). As described above, spring retainer (118) fixedly attaches to a proximal end of outer tube (46) and retains spring stack (116), as shown in FIG. 11. Spring retainer (118) includes a cylindrical sleeve (126) and flange (124) arranged at a distal end of sleeve (126). A proximal portion of sleeve (126) includes threading configured to threadedly receive retaining nut (120). As shown in FIG. 11, spring stack (116) is received over sleeve (126) and is restrained proximally by retaining nut (120) and distally by yoke (114) of translating member (110). Yoke (114) encircles and translates along sleeve (126) to compress spring stack (116) against retaining nut (120) when trigger (32) is actuated.

In the present example, spring retainer (118) couples to outer tube (46) with a snap-fit engagement, such that spring retainer (118) is longitudinally and rotationally fixed to outer tube (46). As shown in FIG. 12, sleeve (126) includes a plurality of circumferentially arranged snap legs (128) having free distal ends configured to lockingly engage outer tube (46). More specifically, as shown in FIGS. 13A and 13B, the free distal end of each snap leg (128) includes a protrusion (130) configured to snap into a corresponding opening (132) formed in the sidewall of outer tube (46). During assembly, the proximal end of outer tube (46) may be inserted into the central bore of spring retainer (118) defined by sleeve (126) and flange (124), and advanced proximally until protrusions (130) snap into openings (132). Various alternative manners of fixing spring retainer (118) to outer tube (46) will be apparent to those of ordinary skill in the art.

Figure 14:
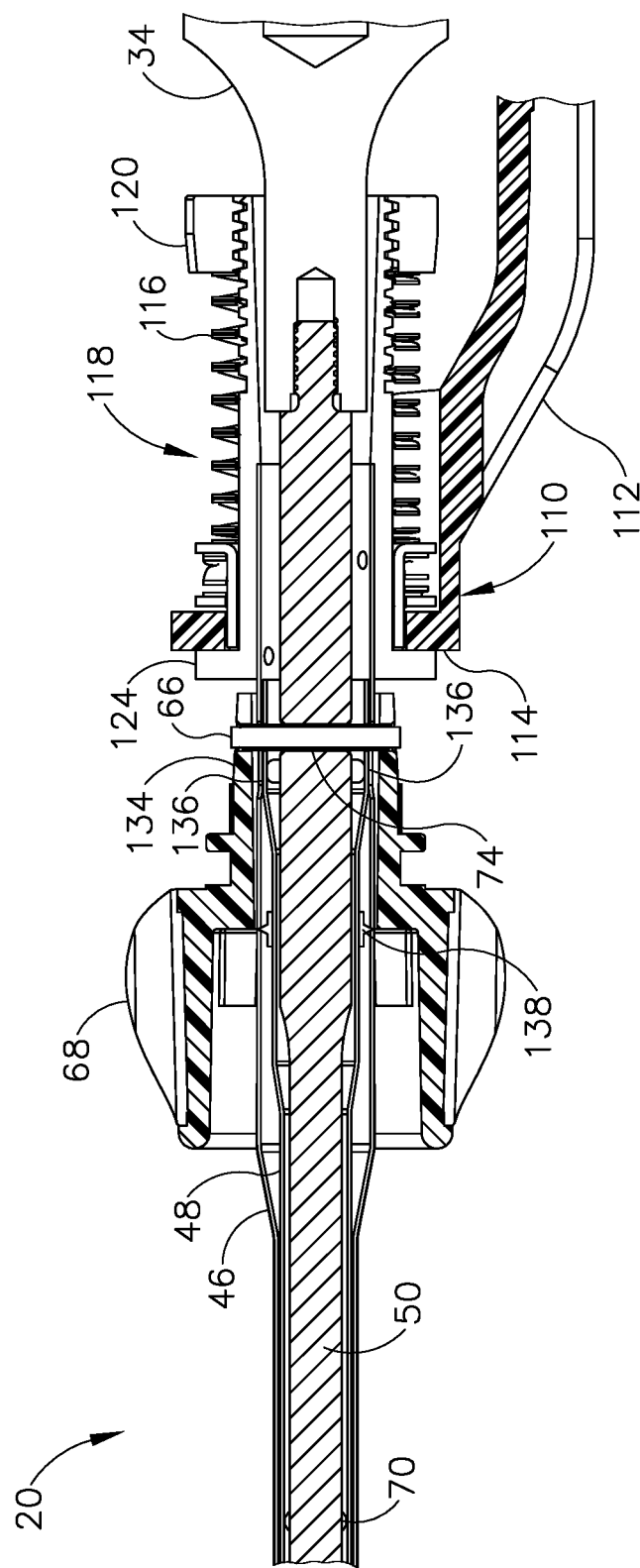
FIG. 14 depicts a partial side sectional view of the surgical instrument of FIG. 1, showing coupling of the shaft assembly, including an ultrasonic waveguide, to the handle assembly.

FIG. 14 shows additional details of shaft assembly (20) and select components of actuation assembly (102) described above, as well as a coupling of a proximal end of ultrasonic waveguide (50) to a distal end of ultrasonic transducer (34). As described above, outer tube (46) is configured to translate longitudinally relative to inner tube (48) and waveguide (50) to move clamp arm (38) between its open and closed positions. In the same configuration, retaining pin (66) extends transversely through a proximal collar (134) of rotation knob (68) and through outer tube, inner tube, and waveguide (50) to thereby secure each of these components rotationally relative to one another, as described above. To accommodate longitudinal translation of outer tube (46) relative to the remaining components of shaft assembly (20), outer tube (46) includes a pair of elongate slots (136) through which retaining pin (66) extends, as shown in FIG. 14. Further, a proximal portion of inner tube (48) may be supported radially within outer tube (46) by a tube support element (138).

In the present example, spring stack (116) is configured to provide a force-limiting feature, such that spring stack (116) resists compression and thereby transfers proximal motion from yoke (114) to outer tube (46) via retaining nut (120) when yoke (114) is driven to actuate outer tube (46) proximally up to a certain force threshold. When clamp arm (38) encounters substantial resistance to further pivotal movement toward ultrasonic blade (36), outer tube (46) will correspondingly provide substantial resistance to further proximal movement, and such resistance will be further provided via retaining nut (120). When this resistance exceeds the predetermined force threshold, and the operator continues to urge trigger (32) toward pistol grip (26), spring stack (116) will begin to compress in response to further proximal motion of yoke (114) while retaining nut (120) and outer tube (46) remain stationary. Spring stack (116) thus absorbs forces that are exerted above the force threshold. Retaining nut (120) may be selectively rotated relative to sleeve (126), via threaded engagement, to compress spring stack (116) against yoke (114) with a desired amount of pre-load. Retaining nut (120) thereby enables adjustability of the predetermined force threshold by allowing adjustment of the pre-load.

D. Exemplary Ultrasonic and Bipolar RF Electrical Circuits

Figure 15A:
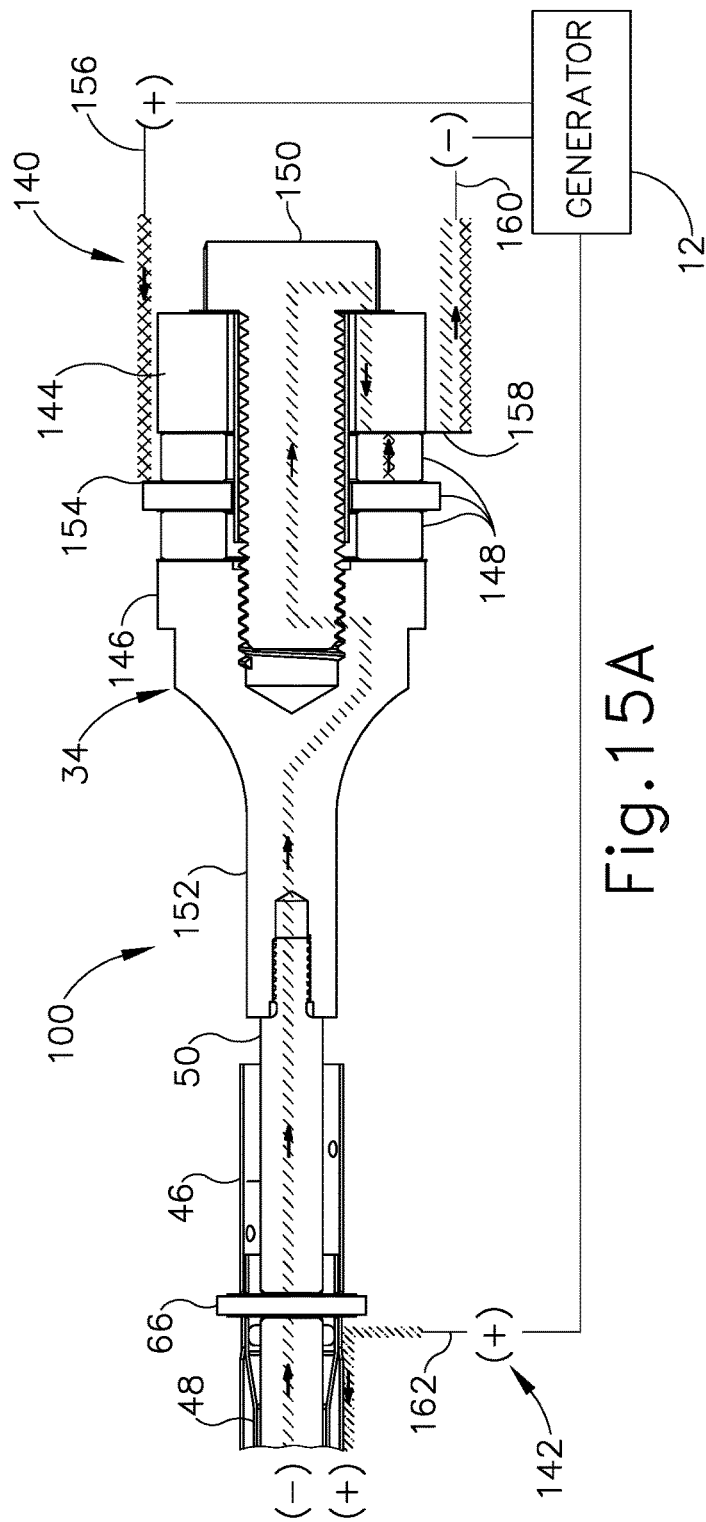
FIG. 15A depicts a schematic view of portions of the surgical system of FIG. 1, showing active and return paths of an ultrasonic electrical circuit and a bipolar RF electrical circuit passing through the surgical instrument.
Figure 15B:
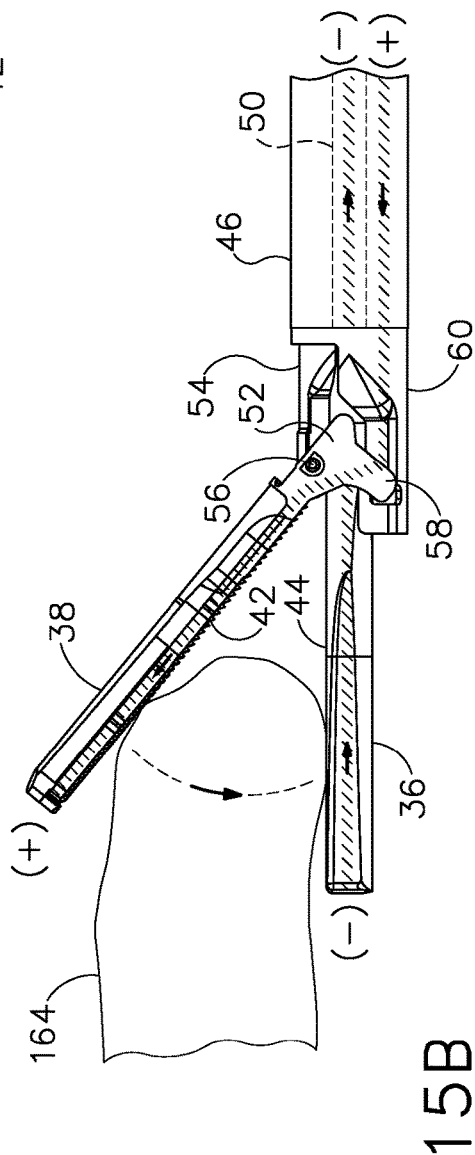
FIG. 15B depicts a schematic view of the end effector of the surgical instrument of FIG. 15A, showing the active path of the RF electrical circuit passing distally from the outer tube to the clamp arm into tissue, and the return path passing proximally from the tissue to the ultrasonic blade and into the waveguide.

FIGS. 15A and 15B show an exemplary configuration of an ultrasonic electrical circuit (140) and a bipolar RF electrical circuit (142) of surgical instrument (14). As shown in FIG. 15A, generator (12) of surgical system (10) is electrically coupled with and configured to energize each of the electrical circuits (140, 142) to thereby enable surgical instrument (14) to deliver ultrasonic energy and electrosurgical bipolar RF energy to tissue. In various examples, generator (12) may energize ultrasonic electrical circuit (140) and RF electrical circuit (142) simultaneously or in selective, alternating manners. Structural components of ultrasonic electrical circuit (140) and bipolar RF electrical circuit (142) are described below, in respective order, followed by a description of electrical current flow through electrical circuits (140, 142). As will be described, electrical circuits (140, 142) may share a common electrical return path.

As described above, acoustic assembly (100) of surgical instrument (14) generally includes ultrasonic transducer (34), ultrasonic waveguide (50), and ultrasonic blade (36). As shown in FIG. 15A, ultrasonic transducer (34) of the present example generally includes a first resonator (or "end-bell") (144), a conically shaped second resonator (or "fore-bell") (146), and a transduction portion arranged between end-bell (144) and fore-bell (146) and comprising a plurality of piezoelectric elements (148). A compression bolt (150) extends distally, coaxially through end-bell (144) and piezoelectric elements (148), and is threadedly received within a proximal end of fore-bell (146). A velocity transformer (152) (or "horn") extends distally from fore-bell (146) and couples with a proximal end of ultrasonic waveguide (50), for example via a threaded connection as shown in FIG. 15A. In exemplary versions, ultrasonic transducer (34) may be further configured in accordance with any of the transducer configurations disclosed in the references incorporated by reference herein.

An active transducer electrode (154) is shown arranged between medial and proximal piezoelectric elements (148), and electrically couples with generator (12) via an active transducer lead (156). A return transducer electrode (158) is shown arranged between end-bell (144) and a proximal piezoelectric element (148), and electrically couples with generator (12) via a return transducer lead (160). An active RF lead (162) is electrically coupled with generator (12), and is shown extending from a proximal portion of outer tube (46). It will be understood that the positioning of active RF lead (162) relative to shaft assembly (20) is exemplary only, and that generator (12) may electrically couple with RF electrical circuit (142) at any suitable location along outer tube (46), or alternatively directly at clamp arm (38) so as to bypass outer tube (46), for example. Moreover, in other examples, active RF lead (162) may electrically couple with inner tube (48) instead of outer tube (46), such that RF electrical circuit (142) passes through inner tube (48) instead of outer tube (46).

As shown in FIG. 15A, ultrasonic electrical circuit (140) includes an active electrical path that passes distally through active transducer lead (156) to active transducer electrode (154) and into piezoelectric elements (148). Ultrasonic electrical circuit (140) further includes a return electrical path that passes proximally from piezoelectric elements (148), through return transducer electrode (158) to return transducer lead (160). Generator (12) directs electrical current through the active electrical path to the return electrical path to thereby energize ultrasonic transducer (34) to produce ultrasonic mechanical vibrations, which are communicated via ultrasonic waveguide (50) to ultrasonic blade (36).

As shown in FIGS. 15A and 15B, RF electrical circuit (142) includes an active RF path that passes from active RF lead (162) to outer tube (46), and distally through outer tube (46) to clamp arm (38) via clevis fingers (58). In the present example, flow of RF electrical energy through the RF active path is enabled by electrical coupling of outer tube (46) with clamp arm (38), for example by metal-to-metal contact. The active RF energy flows from clevis arms (52) into clamp arm electrode (42), and then into tissue (164). As described in greater detail below, clamp arm electrode (42) may be in the form of a clamping-side surface of clamp arm (38), formed integrally with and thereby electrically coupled with the remainder of clamp arm (38). In various examples, the entirety of clamp arm (38), including or not including clamp pad (40), may be formed of an electrically conductive material, such as a metal, such that the entire clamp arm (38) serves as the clamp arm electrode (42).

RF electrical circuit (142) further includes a return electrical path that directs RF energy proximally from end effector (22) to handle assembly (18), via ultrasonic waveguide (50). As shown in FIG. 15B, when tissue (164) is electrically coupled with clamp arm electrode (42) and blade electrode (44) simultaneously, for example by direct or indirect contact, RF energy passes from the active RF path, through tissue (164), to the return RF path, via blade electrode (44). From blade electrode (44), the RF energy returns proximally through waveguide (50) and passes into ultrasonic transducer (34), as described further below. In this manner, tissue (164) is treated with bipolar RF energy provided by generator (12).

In exemplary configurations, blade electrode (44) may be defined by a selected clamping-side surface of ultrasonic blade (36). In other configurations, the entirety of ultrasonic blade (36) may serve as blade electrode (44). In various such configurations, blade electrode (44) is electrically coupled with ultrasonic blade (36), which is electrically coupled with ultrasonic waveguide (50), which in turn is electrically coupled with ultrasonic transducer (34). Accordingly, within the RF return path, RF energy passes proximally from blade electrode (44), through ultrasonic blade (36) to ultrasonic waveguide (50), and ultimately to ultrasonic transducer (34). As shown in FIG. 15A, upon entering ultrasonic transducer (34), the return RF energy passes proximally through forebell (146) and compression bolt (150), and from compression bolt (150) through end-bell (144) to return transducer electrode (158), and to return transducer lead (160). Accordingly, RF electrical circuit (142) and ultrasonic electrical circuit (140) share a common electrical return path through return transducer electrode (158) and return transducer lead (160).

While the exemplary configuration described above employs clamp arm electrode (42) as an active electrode and blade electrode (44) as a return electrode, it will be appreciated that a reverse designation may be employed, in which blade electrode (44) is an active electrode and clamp arm electrode (42) is a return electrode. In such a configuration, the ultrasonic electrical circuit (140) and RF electrical circuit (142) would share a common active electrical path through transducer lead (160) and transducer electrode (158) back to generator (12). Furthermore, in alternative arrangements, RF electrical circuit (142) may pass through inner tube (48) rather than outer tube (46), or RF electrical circuit (142) may bypass inner and outer tubes (46, 48) all together.

As described above, generator (12) may be configured to energize ultrasonic electrical circuit (140) and RF electrical circuit (142) simultaneously, to enable surgical instrument (14) to treat tissue with simultaneous application of ultrasonic energy and electrosurgical bipolar RF energy. Additionally, or alternatively, generator (12) may be configured to energize ultrasonic electrical circuit (140) and RF electrical circuit (142) in alternating manners, to allow for selective application of only one of ultrasonic energy or bipolar RF energy to tissue at a given time. For instance, generator (12) may energize only RF electrical circuit (142) for sealing tissue with bipolar RF energy, leaving ultrasonic blade (36) inactive. Alternatively, generator (12) may energize only ultrasonic electrical circuit (140) for cutting and/or sealing tissue with ultrasonic energy, leaving RF electrodes (42, 44) inactive.

Surgical instrument (14) may include various features for inhibiting undesired electrical shorting of the RF active path and the RF return path of RF electrical circuit (142), for example at locations proximal of clamp arm electrode (42) and blade electrode (44). For instance, retaining pin (66) shown in FIG. 15A may be encased in an electrically insulative sheath (166) that prevents shorting between outer tube (46) and ultrasonic waveguide (50). Similarly, clamp arm pivot pin (56) shown in FIG. 15B may be encased in an electrically insulative sheath that prevents transfer of electrical energy from clamp arm (38) to inner tube (48), which encases ultrasonic waveguide (50). Further, in some examples, select portions of ultrasonic blade (36), ultrasonic waveguide (50), outer tube (46), and/or inner tube (48) may be coated with a layer of electrically insulative material configured to prevent shorting of RF electrical circuit (142).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a shaft; (b) an ultrasonic transducer; (c) a waveguide acoustically coupled with the ultrasonic transducer and extending distally through the shaft; (d) an end effector arranged at a distal end of the shaft, wherein the end effector comprises: (i) an ultrasonic blade acoustically coupled with the waveguide, wherein the ultrasonic transducer is operable to drive the waveguide and the ultrasonic blade with ultrasonic energy, (ii) a clamp arm movable relative to the ultrasonic blade for clamping tissue therebetween, and (iii) an RF electrode operable to seal tissue with RF energy; (e) an ultrasonic electrical circuit operable to energize the ultrasonic transducer, wherein the ultrasonic electrical circuit includes an active path and a return path; and (f) an RF electrical circuit operable to deliver RF energy to the RF electrode, wherein the RF electrical circuit includes an active path and a return path, wherein the return path of the ultrasonic electrical circuit passes through an electrically conductive element, wherein the return path of the RF electrical circuit passes through the electrically conductive element.

Example 2

The surgical instrument of Example 1, wherein the return path of the ultrasonic electrical circuit and the return path of the RF electrical circuit pass through the ultrasonic transducer.

Example 3

The surgical instrument of any of the previous Examples, wherein the ultrasonic transducer comprises: (i) a proximal end element, (ii) a distal end element, (iii) a piezoelectric element disposed between the proximal end element and the distal end element, and (iv) a transducer electrode coupled to the piezoelectric element, wherein the return path of the ultrasonic electrical circuit and the return path of the RF electrical circuit both pass through the transducer electrode.

Example 4

The surgical instrument of Example 3, wherein the ultrasonic transducer further comprises an electrically conductive coupling element that secures the proximal end element relative to the distal end element, wherein the return path of the RF electrical circuit passes through the electrically conductive coupling element.

Example 5

The surgical instrument of Example 4, wherein the electrically conductive coupling element comprises a threaded fastener.

Example 6

The surgical instrument of any of the previous Examples, wherein the end effector includes a first RF electrode and a second RF electrode operable to seal tissue with bipolar RF energy, wherein the RF electrical circuit is operable to deliver bipolar RF energy to the RF electrodes.

Example 7

The surgical instrument of Example 6, wherein the clamp arm provides the first RF electrode, wherein the ultrasonic blade provides the second RF electrode.

Example 8

The surgical instrument of Example 7, wherein the second RF electrode is defined at least in part by a clamping surface of the ultrasonic blade.

Example 9

The surgical instrument of any of the previous Examples, wherein the active path of the RF electrical circuit passes through the clamp arm, wherein the return path of the RF electrical circuit passes through the ultrasonic blade and the waveguide.

Example 10

The surgical instrument of any of the previous Examples, wherein the end effector further comprises a clamp pad secured to the clamp arm, wherein the active path of the RF electrical circuit passes through the clamp pad.

Example 11

The surgical instrument of any of the previous Examples, wherein the shaft is electrically coupled with the clamp arm, wherein the active path of the RF electrical circuit passes distally through the shaft to the clamp arm.

Example 12

The surgical instrument of any of the previous Examples, wherein the shaft comprises an outer tube and an inner tube, wherein active path of the RF electrical circuit passes distally through the outer tube to the clamp arm.

Example 13

The surgical instrument of Example 12, wherein the outer tube is operable to translate relative to the inner tube to actuate the clamp arm relative to the ultrasonic blade.

Example 14

The surgical instrument of any of the previous Examples, wherein the RF electrode is operable to seal tissue with RF energy while the ultrasonic blade treats tissue with ultrasonic energy.

Example 15

A surgical system comprising: (a) a generator; and (b) the surgical instrument of any of the previous Examples, wherein the generator is operable to energize the ultrasonic transducer via the ultrasonic electrical circuit, and simultaneously energize the RF electrode via the RF electrical circuit.

Example 16

A surgical instrument comprising: (a) a shaft; (b) an ultrasonic transducer; (c) a waveguide acoustically coupled with the ultrasonic transducer and extending distally through the shaft; and (d) an end effector arranged at a distal end of the shaft, wherein the end effector comprises: (i) an ultrasonic blade acoustically coupled with the waveguide, wherein the ultrasonic transducer is operable to drive the waveguide and the ultrasonic blade with ultrasonic energy, (ii) a clamp arm movable relative to the ultrasonic blade for clamping tissue therebetween, and (iii) an RF electrode operable to seal tissue with RF energy, wherein the RF electrode is electrically coupled with the ultrasonic transducer.

Example 17

The surgical instrument of Example 16, wherein the RF electrode is provided by one of the ultrasonic blade or the clamp arm.

Example 18

The surgical instrument of any of Examples 16 through 17, further comprising an ultrasonic electrical circuit operable to energize the ultrasonic transducer, and an RF electrical circuit operable to deliver RF energy to the RF electrode, wherein the ultrasonic electrical circuit and the RF electrical circuit each include a return path, wherein the return paths electrically communicate with one another.

Example 19

A surgical instrument comprising: (a) a shaft; (b) an ultrasonic transducer; (c) a waveguide acoustically coupled with the ultrasonic transducer and extending distally through the shaft; and (d) an end effector arranged at a distal end of the shaft, wherein the end effector comprises: (i) an ultrasonic blade acoustically coupled with the waveguide, wherein the ultrasonic transducer is operable to drive the waveguide and the ultrasonic blade with ultrasonic energy, (ii) a clamp arm movable relative to the ultrasonic blade for clamping tissue therebetween, (iii) a first RF electrode provided by the clamp arm, and (iv) a second RF electrode provided by the ultrasonic blade, wherein the first and second RF electrodes are operable to seal tissue with bipolar RF energy.

Example 20

The surgical instrument of Example 19, wherein the second RF electrode is electrically coupled with the ultrasonic transducer.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. patent application Ser. No. 15/967,746, entitled "Combination Ultrasonic and Electrosurgical Instrument Having Slip Ring Electrical Contact Assembly," filed on May 1, 2018, issued as U.S. Pat. No. 10,945,778 on Mar. 16, 2021; U.S. patent application Ser. No. 15/967,747, entitled "Combination Ultrasonic and Electrosurgical Instrument Having Electrically Insulating Features," filed on May 1, 2018, issued as U.S. Pat. No. 10,945,779 on Mar. 16, 2021; U.S. patent application Ser. No. 15/967,751, entitled "Combination Ultrasonic and Electrosurgical Instrument Having Curved Ultrasonic Blade," filed on May 1, 2018, published as U.S. Pub. No. 2018/0333180 on Nov. 22, 2018, issued as U.S. Pat. No. 11,033,316 on Jun. 15, 2021; U.S. patent application Ser. No. 15/967,753, entitled "Combination Ultrasonic and Electrosurgical Instrument Having Clamp Arm Electrode," filed on May 1, 2018, published as U.S. Pub. No. 2018/0333181 on Nov. 22, 2018, issued as U.S. Pat. No. 11,058,472 on Jul. 13, 2021; U.S. patent application Ser. No. 15/967,759, entitled "Combination Ultrasonic and Electrosurgical Instrument Having Ultrasonic Waveguide With Distal Overmold Member," filed on May 1, 2018, published as U.S. Pub. No. 2018/0333183 on Nov. 22, 2018, issued as U.S. Pat. No. 11,051,866 on Jul. 6, 2021; U.S. patent application Ser. No. 15/967,761, entitled "Combination Ultrasonic and Electrosurgical System Having Generator Filter Circuitry," filed on May 1, 2018, published as U.S. Pub. No. 2018/0333184 on Nov. 22, 2018, issued as U.S. Pat. No. 11,304,741 on Apr. 19, 2022; and/or U.S. patent application Ser. No. 15/967,764, entitled "Combination Ultrasonic and Electrosurgical System Having EEPROM and ASIC Components," filed on May 1, 2018, published as U.S. Pub. No. 2018/0333186 on Nov. 22, 2018, issued as U.S. Pat. No. 11,126,661 on Sep. 28, 2021. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. patent application Ser. No. 15/967,758, entitled "Combination Ultrasonic and Electrosurgical Instrument with Clamp Arm Position Input and Method for Identifying Tissue State," filed on May 1, 2018, published as U.S. Pub. No. 2018/0333182 on Nov. 22, 2018, issued as U.S. Pat. No. 11,229,473 on Jan. 25, 2022; U.S. patent application Ser. No. 15/967,763, entitled "Combination Ultrasonic and Electrosurgical Instrument with Adjustable Energy Modalities and Method for Sealing Tissue and Inhibiting Tissue Resection," filed on May 1, 2018, published as U.S. Pub. No. 2018/0333185 on Nov. 22, 2018, issued as U.S. Pat. No. 11,278,340 on Mar. 22, 2022; U.S. patent application Ser. No. 15/967,770, entitled "Combination Ultrasonic and Electrosurgical Instrument with Adjustable Clamp Force and Related Methods," filed on May 1, 2018, published as U.S. Pub. No. 2018/0333187 on Nov. 22, 2018, issued as U.S. Pat. No. 11,266,455 on Mar. 8, 2022; U.S. patent application Ser. No. 15/967,775, entitled "Combination Ultrasonic and Electrosurgical Instrument with Adjustable Energy Modalities and Method for Limiting Blade Temperature," filed on May 1, 2018, published as U.S. Pub. No. 2018/0333188 on Nov. 22, 2018, issued as U.S. Pat. No. 11,229,474 on Jan. 25, 2022; U.S. patent application Ser. No. 15/967,777, entitled "Combination Ultrasonic and Electrosurgical Instrument and Method for Sealing Tissue with Various Termination Parameters," filed on May 1, 2018, published as U.S. Pub. No. 2018/0333189 on Nov. 22, 2018, issued as U.S. Pat. No. 11,229,475 on Jan. 25, 2022; and/or U.S. patent application Ser. No. 15/967,784, entitled "Combination Ultrasonic and Electrosurgical Instrument and Method for Sealing Tissue in Successive Phases," filed on May 1, 2018, published as U.S. Pat. No. 2018/0333190 on Nov. 22, 2018, issued as U.S. Pat. No. 11,259,856 on Mar. 1, 2022. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a shaft assembly including an acoustic waveguide;
   (b) an ultrasonic transducer, comprising:
      (i) a piezoelectric element, and
      (ii) a transducer electrode operatively coupled to the piezoelectric element;
   (c) an end effector distally extending from the shaft assembly including:
      (i) an ultrasonic blade acoustically coupled with the acoustic waveguide, wherein the ultrasonic transducer is operable to drive the acoustic waveguide and the ultrasonic blade with ultrasonic energy,
      (ii) at least one RF electrode configured to seal tissue with RF energy, and
      (iii) a clamp arm movable relative to the ultrasonic blade for clamping tissue therebetween;
   (d) an ultrasonic electrical circuit configured to energize the ultrasonic transducer, wherein the ultrasonic electrical circuit includes an active ultrasonic path and a return ultrasonic path;
   (e) an RF electrical circuit operable to deliver RF energy to the at least one RF electrode, wherein the RF electrical circuit includes an active RF path and a return RF path; and
   (f) an actuation assembly, including:
      (i) an actuation member operatively connected to the clamp arm and configured to selectively direct movement of the clamp arm, and
      (ii) a force-limiting assembly operatively connected between the actuation member and the clamp arm, wherein the force-limiting assembly includes a retainer, wherein the retainer includes a retaining member and a sleeve, wherein the retaining member is adjustably secured along the sleeve for adjusting a predetermined force threshold,
   wherein each of the return ultrasonic path and the return RF path pass through the transducer electrode.

2. The surgical instrument of claim 1, wherein each of the return ultrasonic path and the return RF path pass through an electrically conductive element.

3. The surgical instrument of claim 2, wherein each of the return ultrasonic path and the return RF path pass through the ultrasonic transducer along a common electrical return path portion.

4. The surgical instrument of claim 1, wherein each of the return ultrasonic path and the return RF path pass through the ultrasonic transducer along a common electrical return path portion.

5. The surgical instrument of claim 1, further comprising a return transducer lead extending from the transducer electrode, wherein each of the return ultrasonic path and the return RF path pass through the return transducer lead.

6. The surgical instrument of claim 1, wherein the ultrasonic transducer further includes:
   (i) a proximal end element, and
   (ii) a distal end element,
   wherein the piezoelectric element is disposed between the proximal and distal end elements.

7. The surgical instrument of claim 1, wherein the end effector further includes a clamp arm movable relative to the ultrasonic blade for clamping tissue therebetween.

8. The surgical instrument of claim 7, wherein the shaft assembly includes a first shaft portion operatively connected to the clamp arm and a second shaft portion, and wherein the second shaft portion is selectively movable relative to the first shaft portion to thereby selectively move the clamp arm relative to the ultrasonic blade, wherein the clamp arm includes a first pin, a second pin, and a gap defined therebetween, wherein the first and second pins are connected to the first shaft portion of the shaft assembly, and wherein the ultrasonic blade is configured to be received within the gap.

9. The surgical instrument of claim 7, wherein the shaft assembly further includes an elongate member pivotally connected to the clamp arm, wherein the actuation assembly further includes a yoke operatively connected to the actuation member and configured to move in response to movement of the actuation member.

10. A surgical instrument, comprising:
    (a) a shaft assembly including an acoustic waveguide, wherein the shaft assembly has a first shaft portion and a second shaft portion and the first shaft portion is selectively movable relative to the second shaft portion, wherein the first shaft portion includes an inner tube and the second shaft portion includes an outer tube, wherein the inner tube extends along a longitudinal axis, wherein a distal end of the inner tube is offset radially outwardly relative to the longitudinal axis; and
    (b) an end effector distally extending form the shaft assembly including:
        (i) an ultrasonic blade acoustically coupled with the acoustic waveguide, and
        (ii) a clamp arm movable relative to the ultrasonic blade for clamping tissue therebetween, wherein the second shaft portion is selectively movable relative to the first shaft portion to thereby selectively move the clamp arm relative to the ultrasonic blade, wherein the clamp arm includes:
            (A) a first pin,
            (B) a second pin,
            (C) a gap defined between the first and second pins,
            wherein the first and second pins are connected to the first shaft portion of the shaft assembly, and wherein the ultrasonic blade is configured to be received within the gap.

11. The surgical instrument of claim 10, wherein the first, the second pin, and the gap therebetween extend along a first pivot axis.

12. The surgical instrument of claim 11, wherein the clamp arm includes a first protrusion and a second protrusion connected to the second shaft portion, wherein the first and second protrusion extend along a second pivot axis.

13. The surgical instrument of claim 10, wherein the inner tube includes a distal end and a proximal portion, wherein the clamp arm is spaced further away from the shaft assembly than if the distal end of the inner tube were flush with the proximal portion of the inner tube.

14. The surgical instrument of claim 13, wherein the distal end of the inner tube provides additional lateral clearance between the ultrasonic blade and the first pin.

15. The surgical instrument of claim 14, wherein the additional lateral clearance between the ultrasonic blade and first pin is configured to inhibit contact between the ultrasonic blade and first pin when the ultrasonic blade deflects laterally during back-cutting operations.

16. A surgical instrument, comprising:
    (a) a shaft assembly including an acoustic waveguide and an elongate member;
    (b) an end effector distally extending form the shaft assembly including:
        (i) an ultrasonic blade acoustically coupled with the acoustic waveguide, and
        (ii) a clamp arm movable relative to the ultrasonic blade for clamping tissue therebetween, wherein the clamp arm is pivotally connected to the elongate member; and
    (c) an actuation assembly including:
        (i) an actuation member operatively connected to the clamp arm and configured to selectively direct movement of the clamp arm, and
        (ii) a force-limiting assembly operatively connected between the actuation member and the clamp arm, wherein the force-limiting assembly is configured to limit a clamp force of the clamp arm to a predetermined force threshold, wherein the force-limiting assembly includes a retainer secured relative to the elongate member, wherein the retainer includes a sleeve that has at least one leg radially received within the elongate member to secure the retainer to the elongate member.

17. The surgical instrument of claim 16, wherein the actuation assembly further includes a yoke operatively connected to the actuation member and configured to move in response to movement of the actuation member.

18. The surgical instrument of claim 17, wherein the force-limiting assembly further includes
    a resilient feature captured between the yoke and the retainer, wherein the resilient feature is configured to transmit force from the yoke to the retainer up to the predetermined force threshold such that the yoke and the retainer move together, and wherein the resilient feature is configured to compress at the predetermined force threshold such that the yoke moves relative to the retainer for limiting force at the clamp arm.

19. The surgical instrument of claim 18, wherein the resilient feature includes a spring stack, and wherein the retainer includes
    a retaining member secured to the sleeve, wherein the spring stack is received on the sleeve and captured between the retaining member and the yoke.

20. The surgical instrument of claim 19, wherein the retaining member is adjustably secured along the sleeve for adjusting a predetermined force threshold.

* * * * *